US005679345A

United States Patent [19]

Sanfilippo et al.

[11] Patent Number: 5,679,345
[45] Date of Patent: Oct. 21, 1997

[54] METHOD FOR PREVENTING COMPLEMENT-DEPENDENT REJECTION OF ORGAN OR TISSUE TRANSPLANTS

[75] Inventors: Alfred P. Sanfilippo; William M. Baldwin, III; Robert B. Brauer, all of Baltimore, Md.

[73] Assignee: The Johns Hopkins University, Baltimore, Md.

[21] Appl. No.: 253,279

[22] Filed: Jun. 2, 1994

[51] Int. Cl.$^6$ .................. C07K 16/18; C07K 14/435; A61K 39/395; A61K 38/17
[52] U.S. Cl. .................. 424/130.1; 424/145.1; 530/388.25; 530/389.3; 530/350; 530/380; 530/395; 514/8; 514/12
[58] Field of Search .................. 530/388.25, 389.3, 530/350, 380, 395; 424/145.1, 130.1; 514/8, 12

[56] References Cited

PUBLICATIONS

Jordan et al., 24th Annual Meeting of the American Society of Nephrology, 1991.
Rodey et al., 1989, Transplantation, 48:54.
Snyder, et al., 1966, "Prolongation of renal xenografts by complement suppression," *Surg. Forum.*, 17:478–480.
Ono, et al., 1969, "Improved technique of heart transplantation in rats," *J. Thorac. Cardiovasc. Surg.*, 57:225–229.
Cochrane et al., 1970, "Depletion of plasma complement in vivo by a protein of cobra venom: its effect on various immunologic reactions," *J. Immunol.*, 105:55–69.
Patel, et al., 1971, "Cadaveric kidney transplantation in a patient with donor–specific antileukocyte cytotoxic antibodies," *Transplantation*, 12:88–91.
Podack, et al., 1976, "Purification of the sixth and seventh component of human complement without loss of hemolytic activity," *J. Immunol.*, 116:263–269.
Maroko, et al., 1978, "Reduction by cobra venom factor of myocardial necrosis after coronary artery occlusion," *J. Clin. Invest.*, 61:661–670.
Chartrand, et al., 1979, "Delayed reaction of cardiac xenografts in C6–deficient rabbits," *Immunol.*, 38:245–248.
Podack, et al., 1979, "Structural similarities between C6 and C7 of human complement," *J. Immunol.*, 123:1071–1077.
Rauterberg, et al., 1979, "Isolation of late complement components by affinity chromatography. II. Purification of the human complement component C6," *Immunobiology*, 156:142–152.
Hammer, et al., 1981, "Large scale isolation of functionally active components of the human complement system," *J. Biol. Chem.*, 256:3995–4003.
Kolb, et al., 1982, "Biochemical characterization of the sixth component (C6) of human complement," *Biochem.*, 21:294–301.
Discipio, et al., 1982, "Characterization of human complement components C6 and C7," *Mol. Immunol.*, 19:1425–1431.

Ogata, et al., 1982, "Nucleotide sequence analysis of the complement resistance gene from plasmid R100," *J. Bacteriol.*, 151:819–827.
Granados, et al., 1984, "Genetic polymorphism of the sixth component (C6) of rat complement," *J. Immunol.*, 133:405–407.
Taube, et al., 1984, "Renal transplantation after removal and prevention of resynthesis of HLA antibodies," *Lancet*, (Apr. 14, 1984 pp. 824–826.
Whaley, K., 1985, "Measurement of complement," In *Methods in Complement For Clinical Immunologists*, K. Whaley, ed., Churchill–Livingstone, Edinburgh, United Kingdom, pp. 77–139.
Alexandre, et al., 1985, "Splenectomy as a prerequisite for successful human ABO–incompatible renal transplantation," *Transplant. Proc.*, 17:138–143.
Groggel, et al., 1985, "Role of terminal complement pathway in the heterologous phase of antiglomerular basement membrane nephritis," *Kidney International*, 27:643–651.
Cramer, et al., 1986, "Biochemical markers in rats: linkage relationships of aconitase (Acon–1), aldehyde dehydrogenases (Ahd–2 and Ahd–c), alkaline phosphatase (Akp–1), and hydroxyacid oxidase (Hao–1)," *Biochem. Genet.*, 24:217–227.
Kemp, et al., 1987, "Renal xenograft rejection: prolonging effect of captopril, ACE–inhibitors, prostacyclin, and cobra venom factor," *Transplant. Proc.*, 19:4471–4474.
Adachi, et al., 1987, "Effects of cyclosporine, aspirin, and cobra venom factor on discordant cardiac xenograft survival in rats," *Transplant. Proc.*, 19:1145–1148.
Bannett, et al., 1987, "Experiences with known ABO–mismatched renal transplants," *Transplant. Proc.*, 19:4543–4245.
Auchincloss, Jr., H., 1988, "Xenogeneic Transplantation," *Transplantation*, 46:1–20.
Van de Stadt, et al., 1988, "Discordant heart xenografts in the rat," *Transplantation*, 45:514–518.
Miyagawa, et al., 1988, "The mechanism of discordant xenograft rejection," *Transplantation*, 46:825–830.
Walport, M., 1989, "Complement." In *Immunology*, I. Roitt, J. Brostoff, and D. Male, eds., 2nd ed., CV Mosby Company, St. Louis, Missouri, pp. 13.1–13.16.

(List continued on next page.)

*Primary Examiner*—Frank C. Eisenschenk
*Attorney, Agent, or Firm*—Banner & Witcoff, Ltd.

[57] ABSTRACT

Interference with formation of the complement–based membrane attack complex (MAC) will mitigate or even prevent tissue injury associated with the effects of complement in inflammation and graft rejection. Passive treatment of xenograft recipients at the time of and after transplantation with antibody against C-6, which interrupts the sequence of binding steps that form MAC, has been observed to suppress hyperacute xenograft rejection with no adverse signs or symptoms in the xenograft recipient. The present invention provides a method for interfering with MAC formation in transplant recipients, by administering compounds which interrupt one or more of the binding reactions between C5b and C6–C9, so that the MAC cannot form.

17 Claims, 4 Drawing Sheets

OTHER PUBLICATIONS

Hiemstra, et al., 1989, "Complete and partial deficiencies of complement factor D in a Dutch family," *J. Clin. Invest.*, 84:1957–1961.

Gallin, et al., 1989, "Inflammation," In *Fundamental Immunology*, 2nd. ed., W. Paul, ed., Raven Press, New York, pp. 723–733.

Reding, et al., 1989, "Effect of plasma exchange on guinea pig–to–rat heart xenografts," *Transplant. Proc.*, 21:534–536.

Palmer, et al., 1989, "Removal of anti–HLA antibodies by extracorporeal immunoadsorption to enable renal transplantation," *Lancet*, Jan. 7, 1989, pp. 10–12.

Gracie, et al., 1990, "T cell requirements for the rejection of renal allografts bearing an isolated Class I MHC disparity," *J. Exp. Med.*, 172:1547–1557.

Slapak, et al., 1990, "Renal transplantation across the ABO barrier—a 9–year experience," *Transplant. Proc.*, 22:1425–1428.

Esnault, et al., 1990, "Effect of protein A immunoadsorption on panel lymphocyte reactivity in hyperimmunized patients awaiting a kidney graft," *Transplantation*, 50:449–453.

Taube D., 1990, "Immunoadsorption in the sensitized transplant recipient," *Kidney Int.*, 38:350–358.

Weisman, et al., 1990, "Soluble human complement receptor type 1: In vivo inhibitor of complement suppressing post–ischemic myocardial inflammation and necrosis," *Science*, 249:146–151.

Zhow, et al., 1990, "Prolongation of survival of discordant kidney xenografts by C6 deficiency," *Transplantation*, 50:896–898.

Platt, et al., 1991, "The role of natural antibodies in the activation of xenogenic endothelial cells," *Transplantation*, 52:1037–1043.

Pruitt, et al., 1991, "The effect of soluble complement receptor type 1 on hyperacute xenograft rejection," *Transplantation*, 52:868–873.

Vercellotti, et al., 1991, "Neutrophil adhesion to xenogeneic endothelium via iC3b," *J. Immunol.*, 146:730–734.

Sims, et al., 1991, "The response of human platelets to activated components of the complement system," *Immunol. Today*, 12:338–342.

Thorpe, et al., 1991, "Expression of ABH blood group antigens in human heart tissue and its relevance to cardiac transplantation," *Transplantation*, 51: 1290–1295.

Würzner, et al., 1991, "Functionally active complement proteins C6 and C7 detected in C6– and C7–deficient individuals," *Clin. Exp. Immunol.*, 83:430–437.

Couser, et al., 1991, "C6 depletion reduces proteinuria in experimental nephropathy induced by a nonglomerular antigen," *J. Am. Soc. Nephrol.*, 2:894–901.

White, D.J.G., 1992, "The role of complement in xenograft rejection," *UNOS Update*, 8:6–7.

Adair, J.R., 1992, "Engineering antibodies for therapy," *Immunol. Rev.*, 130:5–40.

Parker, et al., 1992, "Fusion proteins in immunointervention," *Transplant. Proc.*, 24:2362–2365.

Nelson, et al., 1992, "Current experience with renal transplantation across the ABO barrier," *Amer. J. Surgery*, 164:541–545.

Ratkovec, et al., 1992, "Outcome of cardiac transplant recipients with a positive donor–specific crossmatch—preliminary results with plasmapheresis," *Transplantation*, 54:651–655.

Linas, et al., 1992, "Mild renal ischemia activates primed neutrophils to cause acute renal failure," *Kidney Int.*, 42:610–616.

DiScipio, R.G., 1992, "Formation and structure of the C5b–7 complex of the lytic pathway of complement," *J. Biol. Chem.*, 267:17087–17094.

Pramoonjago, et al., 1992, "Role of TraT protein, an anticomplementary protein produced in *Escherichia coli* by R100 factor, in serum resistance," *J. Immunol.*, 148:827–836.

Pruitt, et al., 1993, "The effect of xenoreactive antibody and B cell depletion on hyperacute rejection of guinea pig–to–rat cardiac xenograft," *Transplantation*, 56:1318–1324.

Tavakoli, et al., 1993, "Prolonged Survival of Guinea Pig–to–rat heart xenografts using repeated low doses of cobra venom factor," *Transplant. Proc.*, 25:407–409.

Hayashi, et al., 1993, "Effectiveness of combination therapy using cobra venom factor, splenectomy, and deoxyspergualin in guinea pig to rat cardiac xenografts," *Transplant. Proc.*, 25:405–406.

Xia, et al., 1993, "Effect of repetitive doses of soluble human complement receptor type 1 on survival of discordant cardiac xenografts," *Transplant. Proc.*, 25:410–411.

Leventhal, et al., 1993, "Complement depletion prolongs discordant cardiac xenograft survival in rodents and non–human primates," *Transplant. Proc.*, 25:398–399.

Leventhal, et al., 1993, "The immunopathology of cardiac xenograft rejection in the guinea pig–to–rat model," *Transplantation*, 56:1–8.

Chandler, et al., 1993, "Transplant rejection. Mechanisms and treatment," *Arch. Surg.*, 128:279–283.

Sanchez–Urdazpal, et al., 1993, "Increased bile duct complications in liver transplantation across the ABO barrier," *Ann Surg.*, 218:152–158.

Brauer, et al., 1993, "Rat Strain Differences in Complement Activity Correlate With Hyperacute Rejection of Guinea Pig Cardiac Xenografts," *Transplant. Proc.*, 25:2848–2849.

Takahashi, et al., 1993, "ABO–incompatible kidney transplantation in a single–center trial," *Transplant. Proc.*, 25:271–273.

Pemberton, et al., 1993, "Microvascular effects of complement blockade with soluble recombinant CR1 on ischemia/reperfusion injury of skeletal muscle," *J. Immunol.*, 150:5104–5113.

Brauer, et al., 1993, "Use of C6–deficient rats to evaluate the mechanism of hyperacute rejection of discordant cardiac xenografts," *J. Immunol.*, 151:7240–7248.

Würzner, R., 1993, "Monoclonal antibodies against the terminal complement components," in *Activators and Inhibitors of Complement*, R.B. Sim, ed., Kluwer Academic Publishers, Netherlands, pp. 167–180.

Pruitt, et al., 1994, "The effect of soluble complement receptor type 1 on hyperacute rejection of porcine xenografts;," *Transplantation*, 57:363–370.

Green, et al., 1994, "Antigen–specific human monoclonal antibodies from mice engineered with human Ig heavy and light chain YACs," *Nature Genetics*, 7:13–21.

Kemp, et al., 1994, "Monoclonal antibodies to complement C3 prolong survival of discordant xenografts: guinea pig heart to rat transplantation," *Transplant. Proc.*, 26:1011–1015.

Rollins, S.A., 1994, "Development of an anti–C5 monoclonal antibody as a potent soluble inhibitor of complement–mediated hyperacute rejection." In *Xenotransplantation*, Alexion Pharmaceuticals, Inc., at symposium entitled Strategies for Successful Xenotransplantation, held Jun. 16–17, 1994 in Washington, D.C.

Winkelstein, et al., 1982, "Genetically Determined Deficiency of the Third Component of Complement in the Dog: In Vitro Studies on the Complement System and Complement–Mediated Serum Activities," *J. Immunol.*, 129:2598–2602.

Rosenberg, et al., 1986, "Mice Deficient in C5," in *Progress in Allergy*, Vol. 39, pp. 169–191, (Karger, Basel, 1986).

Hamano, et al., 1991, "The Effect of Intrathymic Injection of Donor Blood on the Graft Versus Host Reaction and Cardiac Allograft Survival in the Rat," *Immun. and Cell Biol.*, 69:185–189.

Groth, et al., 1992, "Evidence of Xenograft Function In a Diabetic Patient Grafted With Porcine Fetal Pancreas," *Transplantation Proceedings*, 24:972–973.

Zanjani, et al., 1992, "Engraftment and Long–Term Expression of Human Fetal Hemopoietic Stem Cells in Sheep Following Transplantation In Utero," *J. Clin. Invest.*, 89:1178–1188.

Srour, et al., 1992, "Sustained Human Hematopoiesis in Sheep Transplanted In Utero During Early Gestation With Fractionated Adult Human Bone Marrow Cells," *Blood*, 79:1404–1412.

METHOD FOR PREVENTING COMPLEMENT-DEPENDENT REJECTION OF ORGAN OR TISSUE TRANSPLANTS

The work leading to this invention was supported in part by Grant Nos. AI19368 and AI01092 from the National Institutes of Health. The United States Government may retain certain rights in this invention.

BACKGROUND

1. Field of the Invention

This invention concerns clinically applicable means of overcoming complement-dependent mechanisms of organ and tissue transplant rejection and related tissue injury.

2. Review of Related Art

Complement is involved in the pathogenesis of tissue injury observed in many immunologically mediated diseases which include systemic lupus erythematosis, rheumatoid arthritis, glomerulonephritis, and immune-hemolytic anemia. Complement is also involved in rejection of transplanted organ grafts. Complement is responsible for much of the tissue injury in transplantation due to inflammatory conditions resulting from rejection or superimposed by infection, ischemia, thrombosis of vessels in the graft, etc., as well as tissue injury due to inflammation from similar causes in patients who have not received an organ transplant. In particular, complement attack on cells is central to the rapid onset phase of immune mediated graft rejection (hyperacute rejection), where complement activation and subsequent tissue damage occur within hours.

Graft rejection may occur through a number of different mechanisms, with the time course of rejection being characteristic of the particular mechanism. Early rejection (hyperacute rejection) occurring within minutes or hours of transplantation, involves complement activation by components that are present at time of the transplant operation. Activation may occur via the classical pathway by preformed antibodies that are reactive with the "foreign" or non-self markers of the graft or via the alternative pathway in response to tissue damage in the graft as a result of, e.g., ischemic damage to the organ during storage before transplantation. Acute rejection occurs days to weeks after transplantation, and is caused by sensitization of the host to the foreign tissue that makes up the graft. Once the host's immune system has identified the transplanted tissue as foreign, all the resources of the immune system are marshalled against the graft, including both specific (antibody and T cell-dependent) responses and non-specific (phagocytic, complement-dependent, etc.) responses. Chronic rejection will usually only occur when the graft recipient is immune suppressed. Then the graft may survive long enough for tissue to undergo changes which ultimately affect survival of the graft. Such changes include hyperplasia and tissue hypertrophy, and endothelial cell damage leading to narrowing of the vascular lumen and potentially impairing the oxygen supply to the graft tissue.

Complement-dependent mechanisms are implicated in failure of organ or tissue grafts by any or all of the following mechanisms:

1) hyperacute rejection of organ xenografts (e.g. pig heart to human).
2) accelerated rejection of ABO incompatible organ allografts.
3) rejection of organ allografts by recipients with performed anti-donor HLA antibodies.
4) refractory forms of accelerated acute rejection of xenografts and allografts.
5) chronic rejection and accelerated graft atheroselerosis of organ allografts and xenografts.
6) organ dysfunction due to prolonged warm ischemia time.
7) lysis of cellular components of a blood, leukocyte, red blood cell or platelet transfusion.

A variety of approaches have been utilized in attempts to prevent or suppress each of these effects, and these attempts are summarized below.

1) Hyperacute rejection currently prevents successful xenotransplantation between phylogenetically distant species. In xenotransplantation between some species combinations, the classical pathway of complement is activated by preformed IgM natural antibodies (NAb), while in others direct activation of the alternative pathway of complement by the endothelium of the xenograft (Xg) appears to be important. The relative contribution to hyperacute rejection (HAR) of the vasoaetive and chemotactic split products of complement (C3a and C5a) versus cell lysis by the membrane attack complex (MAC) formed by C5b-C9 remains to be determined.

Presently there is no clinically applicable means of preventing hyperacute rejection of organ xenografts (Auchincloss, Jr., 1988, *Transplantation*, 46: 1; Platt, et al., 1991, *Transplantation*, 52:1037). Attempts in experimental models have been made to prevent hyperacute rejection by extensive removal of the antibody and depletion of complement using reagent such as cobra venom factor (Leventhal, et al., 1993, *Transplantation*, 56:1-8). Because of the high risk of susceptibility to infection, this approach is not likely to be clinically applicable. Recently, our own work has utilized recombinant soluble complement receptor 1 (sCR1) as a means of abrogating hyperaeute xenograft rejection with success in clinical relevant models (Pruitt, et al., 1994, *Transplantation*, 57:363–370).

Depletion of natural antibodies from rats by B lymphocyte ablation (Pruitt, et al., 1993, *Transplantation*, 56:1315–1318) or plasmapheresis (Van de Stadt, et al., 1988, *Transplantation*, 45:514) does not alone significantly prolong the survival of guinea pig cardiac xenograft in rats. Manipulation of the complement cascade by such techniques as C3 consumption with cobra venom factor (Cochrane, et al., 1970, *J. Immunol.* 105:55; Kemp, et al., 1987, *Transplant. Proc.*, 19:4471; Tavakoli, et al., 1993, *Transplant. Proc.*, 25:407; and Hayashi, et al., 1993, *Transplant. Proc.*, 25:405) or the inhibition of the classical and alternative complement pathway with the human recombinant sCR1 (Pruitt, et al., 1991, *Transplantation*, 52:868; Xia, et al., 1993, *Transplant. Proc.*, 25:410; Pruitt, et al., 1994) is much more effective in prolonging xenograft survival. Unfortunately these approaches to study the dependency of hyperacute rejection on complement in a discordant rodent model have limitations. Complement inhibition as measured by total hemolytic activity (CI-I50) or alternate pathway hemolytic activity (AP50) is incomplete even at high dosages of sCR1 (Pruitt, et al., 1991) or cobra venom factor (Cochrane, et al.). The use of cobra venom factor has the additional drawbacks of generating large amounts of C3a and C5a, which have very potent vasoactive and cherootattic properties (Walport, 1989, in *Immunology*, Roitt, et al., eds., 2nd ed., CV Mosby Company, St. Louis, p. 13). Because complement inhibition could only be temporarily and incompletely maintained in these models, the full contribution of complement to xenograft rejection requires further investigation.

2) Prevention of hyperacute rejection of ABO blood group incompatible allografts has been attempted by use of immunosuppression with antibody depletion by ex vivo plasmapheresis or absorption with specific blood group A or B carbohydrates (Alexandre, et al., 1985, *Transplant Proc.*, 17:138; Bannett, et al., 1987, *Transplant Proc.*, 19:4543; Slapak, et al., 1990, *Transplant Proc.*, 22:1425–1428; Takahashi, et al., 1993, *Transplant Proc.*, 25 (1 Pt 1):271–273). The former technique provides some risk of over immunosuppression (i.e. infection), while the later has only been marginally successful in clinical application.

3) In the case of hyperacute rejection due to performed anti-HLA antibodies, previous attempts at preventing such rejection have been made by using chronic thoracic duct drainage (Patel, et al., 1971, *Transplantation*, 12:88–91) or recipient treatment with extensive plasmapheresis or protein G absorption (Taube, et al., 1984, *Lancet*, 1:824; Palmer, et al., 1989, *Lancet*, 1:10; Esnault, et al., 1990, *Transplantation*, 50:449; Taube, et al., 1990, *Kidney Int.*, 38:350–358; Ratkovec, et al., 1992, *Transplantation*, 54:651). Again, there is such significant expense and risk of infection that the former technique has been discarded, and the later technique has limited application.

4) In cases of accelerated or severe acute rejection involving a humoral component, previous attempts at treatment have included experimental models using newer immunosuppression agents that inhibit humoral responses and plasmapheresis (Ratkovec, et al., 1992). These therapies have proven to be largely ineffective.

5) Chronic rejection remains a poorly understood process affecting a high percentage of kidney and heart allografts. The process of accelerated graft atherosclerosis is thought to involve immune mechanisms that may be related to chronic rejection. At present, no therapy is effective in preventing or reversing chronic rejection.

6) Amelioration of ischemic organ injury: Tissues damaged by warm ischemia can activate complement via the alternative and classical pathway. Complement inhibitors, such as cobra venom factor, decrease reperfusion injury following warm ischemia. (Maroko, et al., 1987, *J. Clin. Invest.* 61:661–670; Weisman, et al., 1990, *Science*, 249:146–151; Linas, et al., 1992, *Kidney Int.*, 42:610–616; Pemberton, et al., 1993, *Immunol.*, 150:5104–5113)

7) Transfusion of blood or blood components from one person or animal to another often leads to antibody production and subsequent lysis of the blood components through activation of complement. Antibody and complement mediated lysis of platelets, red blood cells, or leukocytes is currently the major impediment to transfusion therapy and transfusion support of cancer patients undergoing chemotherapy or radiation therapy.

In summary, prior art therapy for transplant rejection has focused on acute rejection and generally relied on immunosuppression. Prevention of hyperacute rejection requires suppression of complement effects on tissue, which has been attempted either by preventing the initiation of complement activation (e.g., by antibody depletion or plasmapheresis) or by interrupting the complement cascade (e.g., by depleting C3 with cobra venom factor or by inhibiting the C3 convertase with recombinant soluble CR1). Antibody depletion has unacceptable risks of over immunosuppression (i.e., infection), and experimental studies of inhibition of the complement cascade with cobra venom factor or sCR1 show incomplete inhibition. An additional drawback to the use of cobra venom is the prospect of systemic effects due to the large amounts of vasoactive and chemotactic C3a and C5a produced.

In all of the approaches described above, inhibition of complement activity is a key component of the immunosuppressive regimen. However, none of these approaches have been particularly successful. Thus there remains a need for an effective, clinically applicable means of overcoming complement-dependent mechanisms of organ transplant rejection.

SUMMARY OF THE INVENTION

An object of this invention is to inhibit the terminal components of the complement cascade to prevent the inflammatory injury to tissue normally mediated by complement activation stimulated by either the classical or alternative pathways.

Another object of this invention is to provide a method of preventing hyperacute rejection of organs transplanted between animals of incompatible tissue type.

The present invention provides a method for suppressing complement-dependent rejection of organ transplants comprising administering an inhibitor of membrane attack complex formation (MAC formation inhibitor) to an organ transplant recipient in an amount effective to suppress cell lysis initiated by formation of the C5b-C9 membrane attack complex. The MAC formation inhibitor may be a non-functional C6 analog, a non-functional C7 analog, art anti-C6 antibody, an anti-C7 antibody, or the bacterial protein TraT, which inhibits complement-dependent cell lysis at the level of C6. In a particular embodiment, the method of this invention may be used to mitigate damage to an organ graft resulting from alternative pathway activation of complement in a graft recipient's serum by ischemically damaged tissue in the graft organ.

In a particular embodiment, the invention provides a method for mitigating hyperacute graft rejection in a mammal receiving an incompatible organ transplant comprising administering a pharmaceutical composition containing an MAC formation inhibitor, such as an anti-C6 antibody or an anti-C7 antibody, to said mammal in an amount sufficient to prevent hyperacute rejection. The incompatible organ transplants which are subject to hyperacute rejection and which may benefit from treatment according to this invention may be an allograft, a graft with ABO incompatible antigens, a graft with HLA incompatible antigens, or a xenograft.

In another embodiment, this invention provides a method for suppressing complement-dependent lysis of blood components (platelets, erythrocytes, and/or leukocytes) in incompatible transfusions of blood products comprising administering an inhibitor of MAC formation to a transfusion recipient in an amount effective to suppress cell lysis initiated by formation of the C5b-C9 membrane attack complex.

Rats of strains with adequate complement activity reject guinea pig cardiac xenografts hyperacutely (26±12 min.). Using a subpopulation of the PVG strain of rats which are deficient in complement activity [strain PVG(C−)], we have observed that rats which have no measurable complement activity reject their guinea pig cardiac xenografts only after 1–2 days, despite the presence of IgM natural antibodies against guinea pig cells. We have demonstrated that the complement deficiency of PVG(C−) rats involves C6, and that the complement activity can be totally restored by adding purified human C6. Transfer of fresh C6-containing serum to PVG(C−) recipients post-grafting reinstituted hyperacute rejection of guinea pig cardiac xenografts, although heat inactivation of the serum at 56° C. for 30 min. abrogated this effect (correlated with the heat liability of C6 in the rat). These studies indicate that an isolated C6 defect in rats causes a 1-2 day delay in the rejection of a guinea pig cardiac xenograft, demonstrating that modulation of the complement cascade appears to be a very effective method of preventing hyperacute rejection of discordant xenografts.

Passive treatment of recipients with antibody against C-6, which interrupts the sequence of binding steps that form MAC, at the time of and after transplantation resulted in mitigation or prevention of hyperacute xenograft rejection with no adverse signs or symptoms to the recipient. Thus, interference with formation of the complement-based MAC will mitigate or even prevent tissue injury associated with the effects of complement in inflammation and graft rejection. The present invention provides a method for such interference, by administering compounds which interrupt one or more of the binding reactions between C5b and C6-C9, so that the MAC cannot form. Examples of such compounds include monoclonal antibodies that bind either C6 or C7. Although antibodies to human C6 are currently available as monoclonal or polyclonal antibodies, no attempt to utilize such antibodies in preventing or treating rejection of allografts or xenografts has been described prior to our invention.

DETAILED DESCRIPTION OF THE INVENTION

I. Definitions

Figure 1:
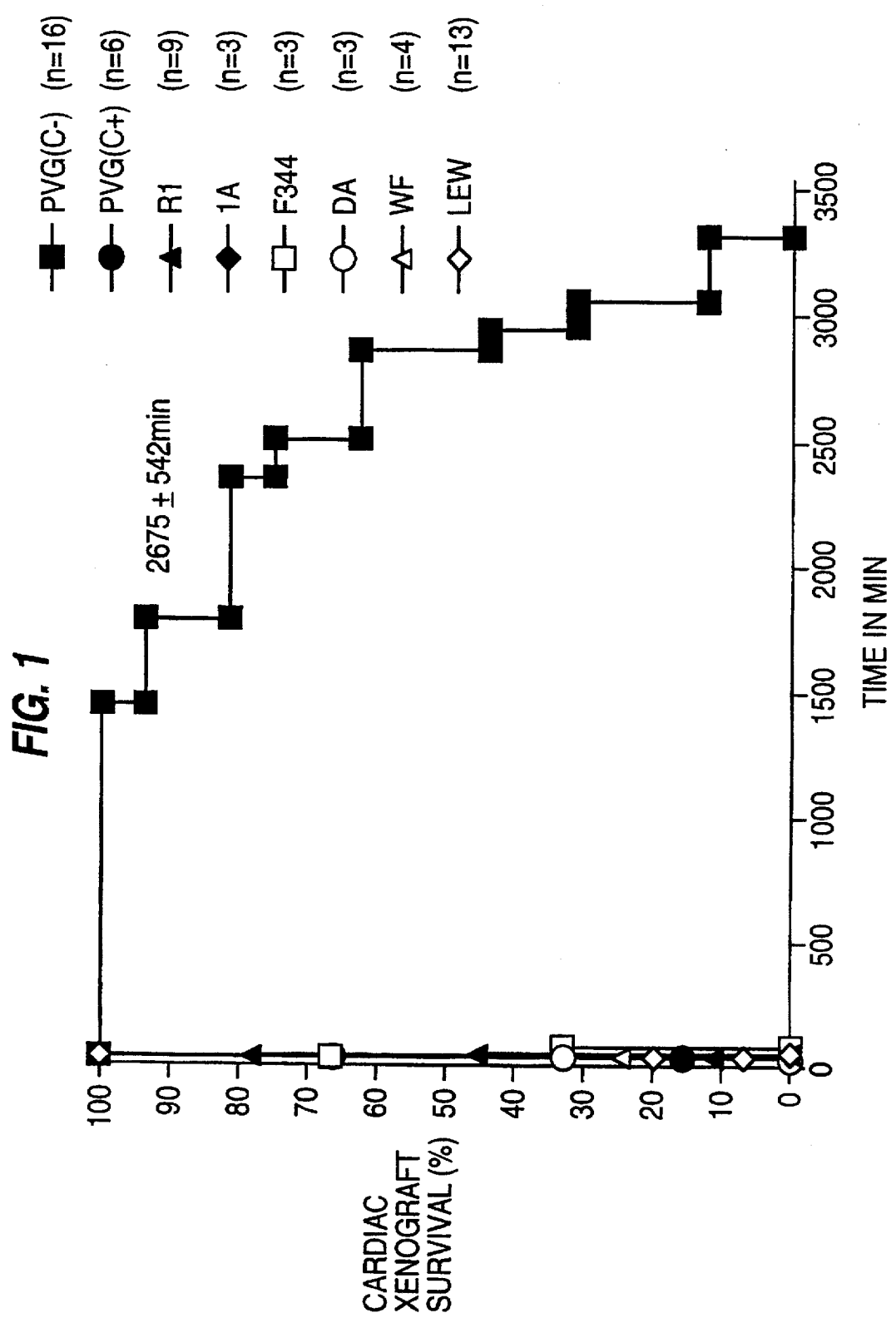
FIG. 1 shows guinea pig cardiac xenograft survival in different strains. All rat strains with easily detectable complement activity in CH50 (total hemolytic activity) and AP50 (alternate pathway complement activity) rejected their guinea pig cardiac xenografts between 15 and 80 min. The C6 deficient PVG(C-) rats rejected their guinea pig cardiac xenografts at an accelerated acute rate between one and two days.

"Human tissue" as used herein is an aggregate of human cells which may constitute a solid mass or a suspension of human cells, such as blood cells, or a human cell line.

The term "antibody" as used herein encompasses whole antibodies made up of four immunoglobulin peptide chains, two heavy chains and two light chains, as well as immunoglobulin fragments.

"Immunoglobulin fragments" are protein molecules related to antibodies, which are known to retain the epitopic binding specificity of the original antibody, such as Fab, F(ab)'$_2$, Fv, etc.

"Passive immunotherapy" involves administration of preformed antibodies to a patient. This is in contrast to "active immunotherapy" where an immunogen is injected into the patient in order to induce the patient to produce antibodies on their own.

A "incompatible" graft is an organ or tissue (such as bone marrow, platelets or red blood cells) which is transplanted into a recipient mammal where the cells of the organ or tissue contain antigens which are recognized by the recipient's immune system as non-self or "foreign" antigens. Incompatible grafts include allografts, (from genetically distinct individuals of the same species), grafts with ABO incompatible antigens, grafts with HLA incompatible antigens, and xenografts (from species distinct from the recipient).

"Complement" is an inclusive term designating a complex group of proteins and glycoproteins found in the blood of vertebrates. These proteins function in the production of inflammation, opsonize foreign materials for phagocytosis, and mediate direct cytotoxicity against various cells. Complement action against cells proceeds by activation of a protease called C3 convertase via one of two pathways: the classic pathway, where binding to an antigen-antibody complex involving IgG or IgM activates C1 which cleaves C2 and C4 to produce a protease that activates C3 by cleaving it to produce C3b; or the alternative pathway, where C3b is produced by a C3 converting protease formed from other complement factors, including Factors B, D, and P, activated by other activators, such as bacterial endotoxin, certain polysaccharides or complexes of antigen with other antibodies. C3b, in complex with activated C2 and C4 or with activated Factor B and P, cleaves C5 to produce C5b which combines sequentially with C6, C7, C8, and C9 to form the "membrane attack complex" (MAC) that is capable of damaging biological membranes.

A "MAC formation inhibitor" is a composition which inhibits binding between two of the five complement components that make up the MAC. In other words, a MAC formation inhibitor prevents formation of the membrane attack complex by interfering with one or more binding steps in the sequential binding of complement components C5b, C6, C7, C8, and C9.

II. Inhibition of MAC formation prevents hyperacute rejection in rats.

Various studies have demonstrated the critical role of complement in hyperacute rejection of xenografts. Decreased complement activity due to genetic deficiencies in C3 deficient guinea pigs (White, 1992, *Unos Update*, 8(9):6), experimental C3 depletion using cobra venom factor (Tavakoli, et al.; Hayashi, et at.; Leventhal, et al., 1993, *Transplant. Proc.* 25:398; Snyder, et al., 1996, *Surg. Forum.*, 17:478; Adachi, et al., 1987, *Transplant. Proc.*, 19:1145), or inhibition of the classical and alternative pathway of complement with sCR1 (Pruitt, et al., 1991; Xia, et. al., 1993; Pruitt, et al., 1994) are associated with significant prolongation of xenograft survival. Treatment with cobra venom factor, which consumes complement by activating C3 systemically, has been reported to prolong guinea pig cardiac xenogrnft survival up to 4 days (Leventhal, et al.). This longer survival may be due in part to the effect of cobra venom factor in reducing participation of C3a and C5a in graft rejection. In contrast, depletion of IgM natural antibodies by plasmapheresis or B cell ablation only minimally prolongs guinea pig cardiac xenograft survival in rats (Pruitt, et al., 1993; Leventhal, et al., 1993, *Transplantation*, 56:1). This probably reflects the contribution of the alternative pathway of complement in this species combination, which may be more important in certain recipient strains than others.

The LEW rat has been the most commonly used recipient for previous xenograft studies. We found LEW rats to have the lowest natural antibodies levels by flow cytometry and others have reported low (Pruitt, et al., 1993; Reding, et al., 1989, *Transplant. Proc.*, 21:534) or not detectable natural antibodies levels (Miyagawa, et al., 1988) in LEW rats by cytotoxic or hemagglutination assays. We found that rat strains with PVG background [PVG(C-), PVG(C+), PVG.R1, PVG. 1A] had consistently higher titers of natural antibodies to guinea pig than did other rat strains.

Guinea pig hearts were transplanted heterotopically to different rat strains after confirming that all rats had IgM natural antibodies to guinea pig cells. Endothelial deposition of split products of C3 would be expected to significantly enhance PMN adhesion to xenograft endothelium and to produce tissue injury (Vercelotti, et al., 1991, *J Immunol.*, 146:730). Deposition of C3b and C5b would be associated with release of C3a and C5a, leading to release of histamine from mast cells and basophils, as well as contraction of smooth muscle and increased permeability of the vessels. In addition, gradients of C5a would contribute to P1VIN accumulation (Gallin, 1989, *Fundamental Immunology*, W. Paul, ed., 2nd ed., Raven Press, New York, p. 723), and the binding of C5a to neutrophils would result in increased adhesion to the capillary endothelium and release of lysosome granules. This chain of events is consistent with the decrease in C3 and C5 activity found in the circulation at 24 h and the prominent infiltrate of PMNs and monocytes observed at the time the xenografts were rejected (1–2 days) by PVG(C-) hosts.

Although we observed deposition of IgM and C3 in guinea pig cardiac xenografts to PVG(C-) rats, these rats did not exhibit hyperacute rejection of the xenograft. Several reports have suggested that PVG rats have low complement activity (Gracie, et al., 1990, *J. Exp. Med.*, 172:1547.; Leenaerts, et al.). We have measured complement levels by the CH50 and AP50 assays in various different rat strains including the PVG strain and its congenic strains R1 and 1A, which only differ from PVG at the RT1.A and the whole MHC locus, respectively. PVG rats from our colony were generally found to have no complement activity in the CH50 and AP50 [PVG(C-)], and this was found to be due to the absence of the C6 component of complement. However, a small number of PVG rats, all of which were phenotyped and found to be RT1$^c$, had significant complement activity in the complement dependent hemolysis assays [PVG(C$^+$)]. These animals are now bred and maintained as separate lines of rats.

A C6 defect blocks a late step in complement activation that is common to the alternative and classical pathway. It has been reported previously that C6 deficient rabbits do not reject puppy hearts (Chartrand, et al., 1979, *Immunology*, 8:245) or cat kidneys (Zhow, et al., 1990, *Transplantation*, 50:896–898) hyperacutely, but the extent of xenograft prolongation could not be established because the experiments were terminated after 5–9 h at which time the grafts were still functioning. The availability of C6 deficient (C-) and sufficient (C+) PVG rats detailed in this study supports the dependency of hyperacute rejection of xenografts on complement.

We have observed that rats with a deficiency in C6 do not hyperacutely reject heart xenografts. Reduced complement activity delayed hyperacute rejection of cardiac xenograft in this discordant rodent model, showing that deficiency of C6 can prevent hyperacute xenograft rejection in rodents. The absence of intravascular platelet accumulation in the guinea pig xenografts to PVG(C-) rats may reflect the dependence on the terminal complement components (C5b-9) of thrombin-mediated platelet aggregation and activation of platelets (Sims, et al., 1991, *Immunol. today.*, 12:338). In addition, the terminal complement components may also have an effect on clotting time in rats, as they do in rabbits (Sims, et al.).

We subsequently demonstrated the ability to produce polyclonal anti-C6 antibodies in rodents. Polyclonal anti-C6 antibodies (of predominately IgG1 subclass which is not complement fixing) were generated by exposing C6-deficient rats to C6. Anti-C6 antibody therapy utilizing these autologous polyclonal antibodies directed against C6 was successful in preventing hyperacute rejection of heart xenografts.

Passive treatment of recipients with antibody against C-6 at the time of and after transplantation have resulted in prevention of hyperacute xenograft rejection. Interference with formation of the complement-based MAC will mitigate or even prevent tissue injury associated with the effects of complement in inflammation and graft rejection for incompatible transplanted organs, including kidney, liver, heart, lung, and pancreas, or incompatible tissue, such as blood, red blood cells or platelets. Thus the procedures of this invention which mitigate the deleterious effects of complement-dependent cell lysis are valuable adjuncts to organ and tissue transplant therapy for mammals with complement in their serum, including humans. The present invention provides a method for achieving such mitigation, by administering inhibitors which interfere with the formation of the MAC (MAC formation inhibitors). Such inhibitors will disrupt the binding of one or more components to the MAC. Preferred MAC formation inhibitors include monoclonal antibodies that bind either C6 or C7. The procedure of this invention can be applied in graft rejection involving pre-formed antibodies to blood group and MAC antigens, as well as in accelerated acute and chronic allograft rejection, and in ischemic injury. Preferred procedures employ monoclonal antibodies of a particular subclass that do not fix complement (such as IgG4 in humans or the IgG1 antibody subclass in the rat) or antibodies modified so that they do not fix complement (e.g., Fab or F(ab')$_2$ fragments).

III. MAC Formation Inhibitors

Any composition which interferes with MAC formation, as measured by hemolytic assays that demonstrate complement-dependent cell lysis, is within the definition of MAC formation inhibitors, as contemplated by this invention. Preferred MAC formation inhibitors include anti-C6 or anti-C7 antibodies. Alternative MAC formation inhibitors include dysfunctional (non-binding) analogs of the complement components which make up the MAC, and bacterial TraT protein, as described below. Where the method of this invention is described below using antibodies against C6, it will be understood that other MAC formation inhibitors may be substituted with similar effect.

a. C-6/C-7 Antibodies

Various C6 or C7 antibodies may be used in the method of this invention, including various antibody isotypes. Antibodies to human C6 are currently available as a monoclonal antibody through Quidell (San Diego, Calif.). Numerous companies sell polyclonal antibodies to human C6. Preferred isotypes include IgG4 which does not itself fix complement.

Alternatively, antibodies to C6 and C7 can be produced by well known methods. The method for producing polyclonal and monoclonal antibodies to C6 is well described and would be similar to that utilized in production antibodies to other human proteins (see, e.g., Rauterberg, et al., 1979, *Immunobiol.* 156: 142–152; Kolb, et al., 1982, *Biochemistry*, 21:294–301; Schreier, et al., "Hybridoma Techniques," 1980; Hammerling, et al., "Monoclonal Antibodies and T Cell Hybridomas," 1980; Kennet, et al., "Monoclonal Antibodies," 1980, all of which are incorporated herein by reference).

Preparation or C6 and C7 as Immunogens

C6 is a $\beta_2$-globulin with an apparent mol. wt. between 95000 and 125000. C7 has been shown by SDS-PAGE to be a single chain with a mol. wt. of 102000. Procedures have been described for simultaneous purification of human C6 and C7 without loss of function (Hammer, et al. (1981), *J. Biol Chem*, 256:3995–4006).

Podack et al. have described methods for isolation of both C6 and C7 from outdated human serum. One report uses sequential ammonium sulfate fractionation, phosphocellulose, and anion-exchange chromatography before and again after gel filtration on Sephadex G-200 (Podack, et al. (1976), *J. Immunol* 116:263–269). This protocol is reported to yield 7% recovery of C6 function with an apparent increase in specific hemolytic activity of 160%, and highly purified C7, shown by SDS-PAGE to be a single chain with a mol. wt. of 102000. C7 was obtained with 160% of the specific hemolytic activity found in serum and with 10% overall recovery. Functional tests for contamination were not reported and immunochemical purity was not demonstrated. An immunochemical approach was subsequently presented that reportedly produced fully active C6 in two steps with more than twice the expected specific hemolytic activity (Podack, et al. (1979), *J Immunol*, 123:1071–1077). This more recent report utilized anti-C7 coupled to Sepharose and a single chromatographic step on QAE-Sephadex. The yield of fully active C7 was improved 2.5-fold. No further information regarding functional or immunochemical purity was presented.

Discipio and Gagnon have also published a procedure for the simultaneous isolation of C6 and C7 (Discipio, et al. (1982), *Mol Immunol*, 19:1425–1531). Using a plasminogen-depleted 5%–12% PEG fraction of outdated human plasma, three sequential chromatographic steps were required to prepare purified C7 with a yield of 15 %. As shown by SDS-PAGE, this C7 was pure, and functional tests indicated that it was free of other terminal component activities of complement. The presence of early classical pathway components, especially C2 which may be a persistent contaminant, was not assessed, however, and the specific activity of the C7 was not reported.

Ranterberg et al. also applied direct immunoaffinity chromatography techniques but used 3M thiocyanate rather than 4M guanidine-HCl for elution of C6 (Rauterberg, et al. (1979), *Immunobiology*, 156:142–152). An antiimpurity column was then used to remove trace contaminants. Their protein was reported to be immunochemically and biochemically pure, with no other terminal complement component functional activity. The yield of fully active C6 was reported to be 12%.

Another immunoaffinity protocol described by Kolb, et al., used 5M guanidine-HCl as the ehant (Kolb, et al. (1982), *Biochemistry*, 21:294–301). C6 was purified to at least twice the expected specific hemolyfic activity. A final antiimpurities step was used to obtain this degree of purification. Yields 48% of the C6 activity in the original serum were reported for this procedure, 2.5 times that recovered by Podack et al. (1976). This difference may be due to the specific antibody preparations used. C6 and C7 for use as immunogens can be readily prepared by these known procedures. Other methods of obtaining these known proteins, or immunogenic fragments of them, will be apparent to those skilled in the art.

Production of Antibodies

Native, recombinant or synthetic C6 or C7 or fragments containing one or more epitopes can be used as the immunogen to produce both polyclonal and monoclonal antibodies. If polyclonal antibodies are desired, the immunogen is used to immunize a selected mammal (e.g., mouse, rabbit, goat, horse, etc.) and serum from the immunized animal later collected and treated according to known procedures. Immunization of mammals, such as rabbits, mice, goats, etc., to produce antibodies is well known in the art.

Polyclonal antibody preparations can be partially purified using immunoaffinity techniques employing a natural, synthetic or recombinant C6 or C7 polypeptide. Such purification methods are well-known in the art. In particular, compositions containing polyclonal antibodies to a variety of antigens in addition to the desired protein can be made substantially free of antibodies which are directed to other antigens by immunoaffinity chromatography. For affinity purification of antibodies, the polypeptide can be coupled to an inert matrix, such as agarose beads. Techniques for such coupling are well known in the art.

Production of non-complement actuating fragments of antibody [Fab or F(ab')$_2$] are well known in the art.

Monoclonal Antibodies

Monoclonal antibodies reactive with C6 or C7 are also readily produced by one skilled in the art. The general methodology for making monoclonal antibodies by hybridomas is well known. Monoclonal antibodies can be raised which are reactive with unique C6 or C7 epitopes. Typically, a rat or mouse is immunized with polypeptide of the present invention, and the rodent will later be sacrificed and spleen cells recovered for fusion with myeloma cells. Particularly preferred rodents are transgenic mice which produce human antibodies, as described in *Nature*, 368:856 (1994), or *Nature Genetics*, 7:13 (1994), which are incorporated herein by reference. Hybrid cells can be selected according to techniques known in the art. Antibody production of each hybrid cell can be screened individually to select antibodies which bind to epitopes on C6 or C7. Panels of monoclonal antibodies produced against C6 or C7 can be screened for various properties, i.e., isotype, epitope, affinity, etc. Of particular interest are monoclonal antibodies of the IgG4 isotype which do not fix human complement. Tests of effectiveness of the antibody would utilize standard techniques of enzyme linked or radio immunoassay, whereas functional affects of such antibodies would utilize standard techniques to reconstitute hemolytic activity to C6 deficient human serum (see, e.g., methods described in Examples 1 and 2 below).

Immortal, antibody-producing cell lines can also be created by techniques other than fusion, such as direct transformation of B lymphocytes with oncogenic DNA, or transfection with Epstein-Barr virus. See, e.g., M. Schreier, et al., "Hybridoma Techniques" (1980); Hammerling, et al., "Monoclonal Antibodies and T-Cell Hybridomas" (1981); Kennett, et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; and 4,493,890, incorporated herein by reference.

Anti-C6 antibodies may be produced by culture of recombinant or transformed cells which express immunoglobulin genes or express immunoglobulin fragments, so long as the immunoglobulin or fragment thereof specifically binds to C6. Particularly preferred monoclonal antibodies will have all or part of their sequence be that of human antibodies. Various procedures for production of human monoclonal antibodies or antibodies that have "humanized" sequences are well known (see, e.g., Adair, JR. "Engineering antibodies for therapy, "*Immunol. Rev.* (1992, 130:5; Chandler, et al. "Transplant rejection. Mechanisms and treatment," *Arch. Surg.* (1993), 128:279; and Parker, et al. "Fusion proteins in immunointervention," *Transplant Proc.* (1992) 24:2362-5, incorporated herein by reference).

The procedures for production of anti-C7 antibodies are similar to those for C6, and a routine matter for the skilled artisan.

b. Dysfunctional C6/C7 Analogs

An additional or alternative method of inhibiting the participation of C6 in the formation of the membrane attack complex is to administer an incompletely functional analog of C6. The complete polypeptide structure of mature C6 consists of 913 amino acid residues. Binding studies have shown that the C5b-binding domain of C6 is located in the 34-kDa carboxyl terminal fragment consisting of two short consensus repeats and two factor I modules (see, DiScipio, 1992, *J Biol. Chem.*, 267(24): 17087-94, incorporated herein by reference). Administration of this fragment of C6 will inhibit the formation of functional MAC at the C6-C7 binding step. The C6 fragment competes with intact C6 for binding to C5b but, once bound, will not bind C7, thus preventing formation of MAC by any C5b molecule bound by the fragment.

Use of such a non-binding C6 analog as the MAC formation inhibitor is particularly interesting, because it permits C6 binding inhibition without the necessity of introducing a "foreign" protein into the graft recipient in the form of a monoclonal antibody. (The fragment can be based on C6 from the same species as the graft recipient.) Similar incompletely functional (non-binding) analogs of C6 or C7 for use as MAC inhibitors can be readily prepared by the skilled worker using the known sequence in view of the structure/function information provided by DiScipio, et al., 1992.

c. Bacterial Products

Certain strains of bacteria are resistant to lysis by complement because they produce TraT protein. This protein has been fully sequenced (Ogata, et al., 1982, *J. Bacteriol.*, 151:819) and has been shown to block complement mediated lysis at the C6 step (Pramoonjago, et al., 1992, *J. Immunol.*, 146:824-836). This bacterial protein and functional equivalents thereof may be used as the MAC formation inhibitor of this invention. It is a routine matter for the skilled worker to obtain a preparation containing the TraT protein, for example, as described by Pramoonjago, et al., 1992, incorporated herein by reference, or by recombinant methods (see, e.g., Sambrook, et al., 1989, "Molecular Cloning: A Laboratory Manual," Cold Spring Harbor) using the sequence information provided by Ogata, et al., 1982, incorporated herein by reference.

Wherever anti-C6 antibodies are referred to herein, equivalent MAC inhibitors are also contemplated.

IV. Therapy a. Conditions subject to treatment by anti-C-6/C-7

The method of this invention may be used to mitigate complement-dependent aspects of organ graft rejection, including any or all of the following:

1) hyperacute rejection of organ xenografts (e.g. pig heart to human).

2) accelerated rejection of ABO incompatible organ allografts.

3) rejection of organ allografts by recipients with performed anti-donor HLA antibodies.

4) refractory forms of accelerated acute rejection of xenografts and allografts.

5) chronic rejection and accelerated graft atherosclerosis of organ allografts and xenografts.

6) organ dysfunction due to prolonged warm ischemia time.

7) lysis of cellular components of blood transfusions.

The effect of anti-C6 and/or anti-C7 antibodies on these rejection phenomena are discussed further below. Similar effects can be expected for other tissue destructive inflammatory reactions by administration of these antibodies.

1) Hyperacute rejection currently prevents successful xenotransplantation between phylogenetically distant species. This process is thought to be initiated by the binding of preformed xenoreactive NAb (natural antibodies), mostly of the IgM isotype to the endothelium of the xenograft followed by activation of the classical pathway of C (complement) (Auchincloss, 1988, *Transplantation*, 46:1.). However, heterologous cell surfaces also may allow stabilization of the alternative pathway C3 convertase leading to activation of the complement cascade and xenograft rejection (Platt, et al.). Administration of MAC formation inhibitors, such as anti-C6 or anti-C7 antibodies, to prevent formation of MAC will mitigate complement-dependent tissue damage whether complement activation occurs via the classic or alternative pathway. Thus the method taught herein may be used to mitigate rejection of transplanted organs between members of different rodent species, as well as between man and other mammalian species where the organs of the two species are of similar size and physiology, by preventing or reducing the extent of hyperacute rejection.

2) Hyperacute rejection of ABO incompatible grafts is well known. See, e.g., Sanchez-Urdazpal, et al., *Ann Surg.*, (1993), 218(2):152-8; Nelson, et al., *Surg*, (1992), 164(5):541-4 (discussion 544-5); Alexandre, et al., *Transplant Proc*, (1985), 17:138; Bannett, et al., *Transplant Proc*, (1987), 19:4543; Slapak, et al., *Transplant Proc*, (1990), 22(4): 1425-8; and Thorpe, et al., *Transplantation*, (1991), 51(6):1290-5. The use of anti-C6 or anti-C7 antibody therapy may be more consistent and effective in preventing hyperacute rejection of ABO incompatible transplants, and would be superior in that it appears to provide no increased risk of infection. C6 or C7 depletion could also be applied in combination with antibody depletion. The successful application of this therapy would be to allow a significant advantage to patients awaiting transplantation where an ABO incompatible live donor is available.

3) Another advantage of anti-C6 or anti-C7 antibody therapy would be to provide a lower risk and more effective means of preventing or treating hyperacute or accelerated acute rejection due to pre-formed antibodies to donor HLA antigens. The successful application of this therapy would permit transplantation to highly sensitized patients for which a compatible donor is not readily identified.

4) In cases of accelerated or severe acute rejection involving a humoral component, previous attempts at treatment have included experimental models using newer immunosuppression agents that inhibit humoral responses and plasmapheresis. Application of the method of this invention as part of a combined therapy to reduce tissue damage caused by acute rejection would permit salvage of a significant number of heart, kidney, liver, lung, pancreas, and other organ allografts otherwise lost to refractory rejection.

5) The process of accelerated graft atherosclerosis is thought to involve immune mechanisms that may be related to chronic rejection. Chronic rejection remains a poorly understood process affecting a high percentage of kidney and heart allografts. The successful application of anti-C6 or anti-C7 antibody therapy would have a significant impact in reducing graft loss due to chronic rejection.

6) Tissues damaged by warm ischemia can activate complement via the alternative and classical pathway. Warm ischemic injury may be incurred during procurement, preservation and transplantation of organs. Similar damage to tissue of the organ can occur as a result of poorly controlled cadaveric blood pressure prior to removal of the organ for transplant. Failure of the graft as a result of such damage could be prevented by treating the recipient with anti-C6 or anti-C7 antibodies after transplantation.

7) When patients are transfused with blood products from a blood donor that is ABO compatible with the patient, the patient will eventually become sensitized to other antigens on the surface of the blood cells. Subsequently, complement activation via the classical pathway will result in MAC lysis of platelets, red blood cells, and/or leukocytes. Administration of MAC formation inhibitors according to this invention will prevent or reduce the extent of lysis of these blood components in the sensitized patient, permitting the use of transfusion therapy in patients requiting multiple transfusions, such as cancer patients undergoing chemotherapy or radiation therapy.

b. Transplant procedures

Organ graft techniques are well known. Three basic stages of organ transplantation are relevant to the potential use of anti-C6 or anti-C7 antibodies. These are: (1) organ recovery, (2) organ preservation, and (3) organ transplantation. Typical transplant procedure is summarized below, and details of the procedures are disclosed in reviews and/or textbooks, such as "Transplantation Procedure," in Sabiston, D. *Text Book of Surgery*, 4th Ed. Saunders, pp. 378–381, or *Principles of Surgery*, Schwartz, et al., eds., 5th Ed., McGraw-Hill, 1989, esp. pp.387–458.

1a. For living kidney donors, the retroperitoneal space is entered directly over the kidney under anesthesia. After the kidney is exposed, the renal artery and vein are dissected to their origin. The ureter is mobilized with its blood supply. The ureter is ligated and divided close to the bladder. The donor renal artery and then the vein are clamped and divided. Blood is flushed from the kidney and cooled with several hundred milliliters of preservation fluid and then immersed in a basin filled with cold electrolyte solution.

1b. For cadaveric donors it is often necessary to maintain optimal circulation which usually requires administration of fluids intravenously. The peritoneal cavity is entered through a midline incision and the aorta and vena cava are exposed. Following dissection of the vascular structures of the organs into the aorta and vena cava for retrograde in situ perfusion. After anticoagulation is achieved with intravenous heparin, the aorta is clamped at the aortic arch and perfusion of cold (4C) preservation solution is initiated through the aortic cannula. The organs rapidly become pale and cold, at which time they are removed from the donor. Further dissection of the individual organ is in a basin of cold solution. Similar procedures for recovery of other organs are well known to the skilled clinician.

2. For transportation the organs are flushed with preservation solution and maintained at 4–10C. For kidneys some centers preserve the kidney on a pulsatile perfusion machine while most prefer simple cooling. Similar procedures for preservation and transportation of other organs are well known to the skilled clinician.

3. The recipient operation varies according to the organ being transplanted. In each case the vessel of the organ to be transplanted are carefully dissected and prepared ex vivo in the basis before being transferred into the recipient to minimize the warm ischemia while the vascular anastomoses between the organ and recipient is performed. These procedures are within the skill of the art.

c. Administration of C6/C7 antibodies in transplantation procedure and recovery.

Various subsystems of the immune system may become involved in rejecting a "foreign" body which an allograft or xenograft represents. The most rapid response (hyperacute rejection) involves activation of complement to form the membrane attack complex (MAC) under appropriate stimuli which will lyse the cells of the graft tissue. For grafts which survive the hyperacute phase, other mechanisms will take over the rejection process, such as NK cells or cytotoxic T cells (acute rejection). On a longer time scale, the immune system will become sensitized to the foreign tissue and mount a coordinated immune attack (chronic rejection).

Hyperacute rejection occurs when complement is activated via the classic pathway by preformed antibodies in the graft recipient that are specific for antigens on the "foreign" tissue of the graft, when these antibodies bind to the graft tissue. Preformed antibodies may be expected in the case of xenografts (natural antibodies), ABO incompatible donor, or HLA incompatible donor. Complement activation by the alternate pathway may also lead to hyperacute rejection, and may occur as a result of tissue injury during surgery to remove the organ from the donor or during surgical implantation in the recipient. Tissue injury that may activate complement can also occur as a result of ischemic events, including the periods of reduced blood flow through an organ from the time it is surgically removed from donor until vascular anastomoses are completed linking the organ to the recipients circulatory system.

In applications involving preformed antibodies (i.e., xenografts, ABO incompatible allografts and performed anti-donor HLA antibodies) MAC formation inhibitors, such as anti-C6 or anti-C7 antibody preparations, may be introduced effectively in one or more of the three basic stages. Likewise, anti-C6 or anti-C7 antibody preparations may be introduced as soon as the potential for organ damage due to poorly controlled cadaveric blood pressure or a prolonged warm or cold ischemia time is recognized. In cases of refractory accelerated acute rejection of xenografts and allografts or chronic rejection and accelerated graft atherosclerosis, the anti-C6 or anti-C7 antibody preparation may be administered as one component of the rejection therapy.

Anti-C6 or anti-C7 antibodies may be administered to the organ donor or infuse it into the isolated organ to remove any C6 or C7 that might be used in subsequent MAC formation. However, the C6 and C7 that are incorporated into the MAC come principally from serum of the organ recipient, and preferred therapeutic procedures will include introduction of the MAC formation inhibitor into the circulatory system of the graft recipient during or after the surgical transplantation procedure, most preferably both during and after surgery.

d. Formulating MAC Formation Inhibitors.

For therapy according to the method of this invention, MAC formation inhibitors, such as anti-C6 and C7 monoclonal antibodies, may be formulated in a pharmacologically acceptable solution or suspension, which is preferably a physiologically-compatible aqueous solution, or in coated tablets, tablets, capsules, suppositories or ampules, as described in the art, for example in U.S. Pat. 4,446,128, incorporated herein by reference. Anti-C6 and anti-C7 antibodies are preferably formulated in pharmaceutical compositions containing the antibody and a pharmaceutically acceptable carrier. The pharmaceutical composition may contain other components so long as the other components do not reduce the effectiveness of the anti-C6 or anti-C7 antibody so much that the therapy is negated. Pharmaceutically acceptable carriers are well known, and one skilled in the pharmaceutical art can easily select carriers suitable for particular routes of administration (see, e.g. *Remington's Pharmaceutical Sciences*, Mack Publishing Co., Easton, Penna., 1985).

e. Dosing and Monitoring

Dose and duration of therapy will depend on a variety of factors, including mode of administration, the patient age, patient weight, and tolerance of the antagonist. The pharmaceutical composition is preferably administered to a mammal in an amount sufficient to suppress complement-dependent inflammatory response in the mammal. The pharmaceutical compositions containing MAC formation inhibitors according to this invention may be administered by parenteral (subcutaneous, intramuscular, intravenous, intraperitoneal, intrapleural, intravesicular or intrathecal), topical, oral, rectal, or nasal route. Intravenous or intramuscular administration are preferred, being the most efficient routes for introducing the MAC formation inhibitor to the bloodstream. A typical initial dose for administration would be 10–100 micrograms per kilogram of the anti-C6 or anti-C7 antibody, when administered intravenously, intramuscularly or subcutaneously, although this amount may be adjusted by a clinician supervising the administration (as commonly occurs in the administration of other immune suppressive agents which reduce rejection). A single administration may usually be sufficient to prevent hyperacute rejection, but multiple administrations may be carried out to supplement anti-rejection therapy at later stages.

The dose of a particular drug and duration of therapy for a particular patient can be determined by the skilled clinician using standard pharmacological approaches in view of the factors described herein. Initial dose levels are typically selected based on their ability to achieve ambient concentrations shown to be effective using in vitro models, such as inhibition of complement-dependent hemolytic activity measured as described in Example 1 below, and in vivo models, such as the xenotransplantation model described in Example 3 below, and in clinical trials, up to maximum tolerated levels. Dose and route of administration of anti-C6 or anti-C7 antibodies will generally be chosen to achieve serum concentrations of the antibody of from about 0.1 µg/ml to about 100 µg/ml.

Standard procedure in transplantation therapy requires that immune suppressive therapy be tailored to the individual patient and the circulatory concentration of the chemotherapeutic agent be monitored regularly. The response to treatment may be monitored by analysis of complement activities in the blood or body fluid of the patient, measurement of anti-C6 or anti-C7 levels directly in the blood or other body fluids, or monitoring other graft rejection indicators in the patient. A minimum preferred amount for administration is the amount required to suppress MAC formation to a level at which cell lysis is minimized. Cell lytic activity in the serum of the graft recipient may be monitored by standard hemolytic assays (e.g., CH50 assay described herein). Alternatively, sensitive sandwich enzyme linked immune sorbant assays (ELISAs) based on monoclonal antibodies directed to native C6 and C7 allow the detection and quantitation of these complement proteins in patient samples (see Wurzner, et al., 1991, *Clin Exp. Immunol.*, 83(3):430-7, incorporated herein by reference). However, antibodies to these complement proteins (or analogs of the proteins) may interfere with immunoassay, so hemolytic assays are preferred.

The effectiveness of therapy with MAC formation inhibitors will also be monitored by changes in clinical and pathological criteria. Kidney, heart and liver transplant rejection are diagnosed most reliably by pathological changes in biopsies of the graft. Several clinical criteria indicate the need to perform a biopsy and support the diagnosis. These criteria include clinical signs and symptoms, laboratory assessment of blood and urine, and ultrasonography. For example, kidney graft rejection is usually accompanied by decreased urine output with increasing serum creatinine values. Suitable mitigation of rejection of a kidney graft may be recognized based on significant decrease in serum creatinine (preferably to less than 2 mg/dl), and increased urine output. Heart and liver transplant rejection are accompanied by changes in the electrocardiogram and hepatic enzymes, respectively.

The skilled clinician will adjust the dose and duration of therapy based on the response to treatment revealed by the above criteria. It is preferable to administer the MAC formation inhibitors at higher rather than lower levels. C6 deficiency is associated with very limited secondary morbidity. This most frequently is neisserial infections which could be easily prevented with appropriate antibiotics during anti-C6 treatment.

Treatment according to the method of this invention will not necessarily prevent all aspects of rejection, but it will be effective to suppress the complement-dependent component of transplant rejection. Even partial suppression of rejection is beneficial, because mitigation of the rejection phenomena will allow rescue of some of the tissue in the graft in a viable state. For example, even a partially functioning kidney may permit the recipient to avoid dialysis or prolong the periods between dialysis, even if some MAC-dependent cell lysis has occurred. Similarly, a fully functional heart graft is preferable, but mitigation of rejection sufficient to permit some increase in exertion by the recipient, relative to the recipient's state before transplant, is valuable. Partial rescue of liver tissue in a liver graft undergoing rejection is also valuable because the remaining viable liver tissue can recover and regenerate while the patient is supported with coagulation proteins and other substances normally produced by the liver.

MAC formation inhibitors may be administered to a patient undergoing transfusion therapy to suppress complement-dependent lysis of platelets, red blood cells, and/or leukocytes, in accordance with the procedures described above. Preferably the MAC inhibitor is administered to achieve reduction of the standard hemolytic activity (e.g., CH50) of the patient's serum by about an order of magnitude or greater. The MAC formation inhibitor will usually be administered to the patient before or at the time of the transfusion, so that lysis of the blood components introduced by the transfusion is reduced.

Modifications of the above-described modes for carrying out the invention that are readily apparent to persons of skill in medicine, immunology, hybridoma technology, pharmacology, and/or related fields are intended to be within the scope of the following claims. All publications and patent applications mentioned in this specification are indicative of the level of skill of those skilled in the art to which this invention pertains. All publications and patent applications identified herein are incorporated by reference to the same extent as if each individual publication or patent application was specifically and individually indicated to be incorporated by reference.

EXAMPLES

In order to facilitate a more complete understanding of the invention, a number of Examples are provided below. However, the scope of the invention is not limited to specific embodiments disclosed in these Examples, which are for purposes of illustration only.

Example 1

Hyperacute Xenograft Rejection is Absent in C6 Deficient Rats

In this study, genetically determined differences in C6 activity were correlated with hyperacute rejection of guinea pig (GP) cardiac xenografts by the rat.

Animals

Inbred male virus free Hartley guinea pigs, 8–12 weeks of age from Charles River (Wilmington, Mass.) served as cardiac xenograft donors. Male, PVG(C−) (RT1.$A^cB^c$), PVG(C+) (RT1.$Ac^Bc$), PVG.R1 (R1) (RT1.$A^aB^c$) on a PVG background, PVG. 1A (1A) (RT1.$A^aB^a$) on a PVG background and DA (RT1.$A^aB^a$) rats were bred in our own isolated colony. PVG(C−) rats were also obtained from Bantin & Kingman (Freemont, Calif.). F344 (RT1$^{1v1}$) and Wistar/Furth rats (W/F) (RT1$^1$) were purchased from Harlan Sprague Dawley (Indianapolis, Ind.), and LEW rats (RT1$^1$) from Charles River. All rats were 12–16 weeks old when used as recipients.

Complement hemolytic activity

Each rat was tested for complement activity in CH50 and AP50 prior to xenografting. Seven different rat strains were tested for complement activity and 6 strains [PVG.R1 (R1), PVG. 1A (1A), DA, W/F, F344, LEW] had readily detectable complement activity in the total (CH50) and alternative pathway (AP50).

Complement activity assays

A modification of the technique described by Whaley (Whaley, 1985, in *Methods in Complement for Clinical Immunologists*, K. Whaley, ed., Churchill-Livingstone, Edinburgh, p. 77) for measuring the total hemolytic activity (CH50) and alternative hemolytic activity (AP50) was used. Sheep red blood cells (SRBC) 0Diamedix, Miami, Fla.) were sensitized with rabbit anti-SRBC serum diluted 1:100 (Accurate, Westbury, N.Y.). For the AP50, uncoated guinea pig RBCs were used. RBC for both assays were added to serially diluted serum samples in 96-well U-bottomed plates, in triplicate. After incubation at 37° complement for 60 min., plates were centrifuged at 1100 g at 4° C., for 5 min. Supernatants were transferred to fresh 96-well plates to measure the hemoglobin (Hgb) released by optical density (OD) at 405 nm with a Titertek MK II automated scanner (Flow Laboratories, McLean, Va.). The percent maximal Hgb release was calculated for each dilution as follows:

% max Hgb release =

$$\frac{(\text{mean } OD_{sample} - OD_{diluted\ sera} - OD_{spontaneous\ Hgb})}{(OD_{Hgb\ max\ in\ H2O} - OD_{spontaneous\ Hgb})} \times 100$$

CH50 and AP50 were defined as the serum dilution yielding 50% maximal Hgb release.

R1, 1A, F344, DA and LEW strain rats had easily detectable complement activity that ranged in titer between 90–150 for the CH50 and between 6–24 for the AP50. In contrast, all PVG rats which were obtained from Bantin & Kingman (n=10) and most PVG rats which were bred in our own colony had no detectable complement activity [PVG (C−)] in both assays. Upon screening a large number of PVG rats (n=100) from our colony, about 5% of the PVG rats were found to have normal CH50 and AP50 levels [PVG (C+)]. Each of the PVG(C−) and PVG(C+) rats were phenotyped and found to express the appropriate RT1.$A^c$ antigens (data not shown).

Extensive breeding studies of PVG(C+) and PVG(C−) rats and their F1 (PVG(C−/C+) progeny showed that the complement sufficiency was inherited as a single autosomal dominant gene and the deficiency was an autosomal recessive gene. Because all of the R1 rats (which are congenic to the PVG, differing only at the RT1.A region) had high complement activity, we wanted to determine whether the complement deficiency was linked to RT1.A. F1 progeny from PVG(C−) rats and R1 all had normal CH50 levels and when these F1 rats were backcrossed to PVG(C−) parents, no linkage was found between RT1.A phenotype and complement deficiency (Table 1).

TABLE 1

Two by two table of backcrossed (R1 × PVG(C−)) F1 with PVG(C−), shows no linkage of C− deficiency with RT1.A phenotype

|     | a/c | c/c |
| --- | --- | --- |
| C−  | 7   | 2   |
| C+  | 7   | 3   |

On the basis of allotype markers, C6 has been reported to be in linkage group X1 in the rat (Cramer, et al., 1986, *Biochem. Genet.*, 24:217; Granados, et al., 1984, *J. Immunol.*, 133:405.). Although the location of linkage group XI has not yet been defined, it differs from the RT1 rat major histocompatibility complex (MHC), which is in linkage group IX. This is consistent with our observation that the complement defect in PVG rats (RT1$^c$) segregates independently of RT1 in breeding experiments with R1 rats (RT1.$A^a$).

Analysis of complement deficiency

Representative serum samples of PVG(C−) rats from Bantin & Kingman (n=3) and our own colony (n=4) and PVG(C+) (n=2) were tested for levels of C6 and factor B.

Immunodiffusion

Factor B was determined by rocket-electrophoresis using monospecific antisera (Hiemstra, et al., 1989, J. Clin. Invest., 84:1957). Rabbit anti-rat factor B was diluted 1/30 an a 2% agarose solution. Subsequently, agarose gels were poured onto slides and allowed to set. Wells were punched in the agarose and filled with a ½ dilution of PVG(C+) or PVG(C−) serum. The samples were subjected to electrophoresis for 16h at 20 mA and rinsed in phosphate buffered saline (PBS) containing 2 mM EDTA. Precipitin arcs were visualized with Coomassie Brilliant Blue and rocket heights were compared between PVG(C+) or PVG(C−) serum.

Analysis of C6 deficiency

Rat C6 was assessed by specific hemolytic assays using EA (sheep red blood cells coated with subagghtinating amounts of rabbit anti-sheep erythrocyte IgG) and C6-deficient human serum as described previously (Leenaerts, et al., 1993, *Clin. Exp. Immunol.*, in press.). Briefly, rat serum samples were diluted in DGVB$^{++}$ (half-isotonic Verona buffered saline containing 0.05% gelatin, 0.15 mM $CaCl_2$+0.5 mM $MgCl_2$ and 3% dextrose). For C6 determinations, 0.1 ml portions were incubated together with 0.1 ml EA in DGVB$^{++}$ (1×10$^8$ cells/ml) containing a 1/100 dilution of C6 deficient human serum for 60 min. at 37° C. Hemolysis was measured in a Beckman photo spectrometer as absorbance at 414 nm of the supernatant obtained after centrifugation. The number of effective hemolytic sites generated (Z) was calculated and expressed as percentage consumption relative to pooled normal PVG(C+) serum.

PVG(C−) rats from Bantin & Kingman and our own inbred colony were found to have less than 3% of C6, but had normal serum levels of Factor B when compared to congenic R1 rats. PVG(C+) rats from our colony had 80% of C6 as compared to 129% for R1 rats based on a pooled rat serum C6 standard (Table 2).

TABLE 2

| Serum concentration of complement factors C6 and Factor B | | | |
|---|---|---|---|
| | (n) | C6 (%) | B (%) |
| PVG(C−) B&K | 3 | 2.7 | 65 |
| PVG(C−) Colony | 4 | 2.5 | 82 |
| PVG(C+) Colony | 2 | 85 | 72 |
| PVG.R1 | 1 | 129 | 100 |

The addition of purified human C6 (Sigma, St. Louis, Mo.) reconstituted hemolytic activity to PVG(C−) serum. Because human C6 has been reported to be heat stabile (Kolb, et al., 1982, Biochem., 21:294), the heat stability of rat C6 was tested. Hemolytic titration of C6 was performed in heated (56° C. for 30 min.) and non-heated (0° C. for 30 min.) normal rat serum using C6 deficient human serum (1/100) and EA targets. The number of effective hemolytic sites generated (Z) was calculated and expressed as percentage consumption relative to pooled normal PVG(C+) serum. Normal rat serum reconstituted C6 deficient human sera in a dose dependent manner. Heat inactivation totally eliminated this effect, indicating that rat C6 is heat labile.

Preoperative serum characterization

Preoperative serum samples were collected by heart puncture using a 1 ml tuberculin syringe. Blood was allowed to clot for 30 min. at 37° complement and then 1 h on ice. Following centrifugation at 4° complement and 1100 g, serum was aspirated and stored in aliquots at −80° C. until use.

Preoperative MHC phenotyping

The MHC phenotype of each PVG recipient was confirmed by labeling PBLs with the RT1.A$^c$ specific monoclonal antibody (MAb) YR.5/12 (Serotec, Bicester, UK). The RT1.A$^1$ specific MAb WFL4F12.3, and RT1.A$^a$ specific MAb MN4 (ATCC, Rockville, Md.) served as negative controls. Binding was measured by flow cytometry.

Flow cytometric analysis

2×10$^5$ lymphocytes were placed in 12×75 mm plastic tubes in 50 μl of PBS, pH 7.4 containing 0.1% sodium azide and 2% bovine serum albumin (Sigma, St. Louis, Mo.). Serial dilutions of serum or MAbs (50 μl) were added and incubated for 30 min. at 4° C. The cells were then washed twice and 50 μl of fluorescein isothiocyanate (FITC) or phycoerythrin labeled Ab was added. After incubating 30 min. at 4° C., the cells were washed twice, resuspended in PBS containing 1% formalin, and analyzed using a FACScan™ flow cytometer (Beeton-Dickinson, Mountain View, Calif.).

Preoperative IgM natural antibodies antibody titers

Guinea pig-specific rat IgM natural antibodies levels in preoperative serum samples were measured by flow cytometry using guinea pig lymphocytes as target cells and a phycoerythrin-conjugated goat antibody specific for the μ chain of ra IgM (Jackson Immunoresearch Labs, West Grove, Penna.) (dilution 1:100) as a detecting reagent. The titer was expressed as the last serum dilution yielding a signal 5 channels above background. All rat strains tested had easily detectable IgM natural antibodies to guinea pig leukocytes, but there was considerable variation among the different strains. PVG(C−) rats had the highest titer of IgM natural antibodies (96±36); PVG(C+), while its congenic R1 and 1A trains had intermediate titers (64) and the other strains tested had low titers (16–32).

Median titer ±SD of CH50, AP50 and IgM natural antibodies titers of different rat strains ranged between 150 and 5, except for PVG(C−) rats, which had no detectable complement activity but the highest titer of IgM natural antibodies.

Xenograft survival

Under halothane anesthesia, heterotopic cardiac xenotransplantation was performed using the microsurgical technique of Ono and Lindsey (Ono, et al., 1969, J. Thorac. Cardiovasc. Surg., 57:225), with anastomosis of the donor aorta to the recipient infrarenal aorta and the donor pulmonary artery to the recipient infrarenal vena cava. Cardiac xenografts were evaluated visually over the first 45 min. following reperfusion, and after abdominal closure, every 60 min. by abdominal palpation until rejection. Rejection was defined as total cessation of contractions and was confirmed by direct visualization and histologic examination of the cardiac xenograft.

Some PVG rats had adequate complement activity [PVG(C +)] but others [PVG(C−)] had a profound deficiency of C6. All rats with adequate complement activity, including the R1 and 1A strains which only differ from PVG at the MAC class I and full MHC loci, respectively, rejected their guinea pig cardiac xenografts hyperacutely between 15 and 80 min. PVG(C+) (RT1$^c$) rats also rejected guinea pig cardiac xenografts hyperacutely (26±12 min.; n=6), whereas PVG(C−) (RT1$^c$) rats, which had the highest natural antibodies titer, rejected heterotopic guinea pig cardiac xenografts in 1–2 days (2678±542 min.; n=16).

Survival of guinea pig cardiac xenografts in the different rat strains is shown in Table 3 and illustrated in FIG. 1. All R1 (n=9), 1A (n=3), F344 (n=3), DA (n=3), W/F (n=4) and LEW (n=13) recipients rejected their xenografts hyperacutely between 5 and 80 min. In contrast, PVG(C−) rats rejected their guinea pig cardiac xenografts in 2678±542 min. (n=16) with an acute inflammatory infiltrate. Six of the PVG(C+) rats were used as transplant recipients and rejected their guinea pig cardiac xenografts hyperacutely in 26±12 min., indicating that the complement system plays an important role in this discordant xenograft rejection. There was no significant correlation between IgM natural antibodies titers against guinea pig lymphocytes and guinea pig cardiac xenograft survival within any group.

TABLE 3

| Guinea Pig-To-Rat cardiac Xg survival | | |
|---|---|---|
| Rat strain | Graft survival (min) | Mean ± SEM |
| PVC(C−) | 1440, 1740, 1860, 2340, 2580, 2640, 2820, 2880, 2880, 2910, 2940, 3050, 3060, 3060, 3300, 3360 | 2675 ± 542 |
| PVG(C+) | 13, 15, 23, 29, 29, 50 | 26 ± 12 |
| PVG.R1 | 22, 24, 25, 26, 33, 35, 35, 35, 40, 55 | 33 ± 10 |

TABLE 3-continued

Guinea Pig-To-Rat cardiac Xg survival

| Rat strain | Graft survival (min) | Mean ± SEM |
|---|---|---|
| PVG.1A | 20, 27, 47 | 31 ± 14 |
| F344 | 16, 22, 80 | 40 ± 29 |
| DA | 14, 20, 23 | 19 ± 04 |
| W/F | 14, 15, 18, 67 | 28 ± 22 |
| LEW | 5, 7, 7, 9, 9, 10, 11 16, 17, 24, 40, 60 | 17 ± 15 |

Histologic evaluation

Portions of cardiac xenografts collected at the time of rejection or sacrifice were fixed in 10% formalin, embedded in paraffin, sectioned, and stained using hematoxylin and eosin (H&E). Xenografts were evaluated for intravascular platelet aggregation, congestion, vessel disruption, interstitial hemorrhage, myocardial necrosis and leukocyte infiltration using a histological grading from 1–3$^+$.

Figure 2:
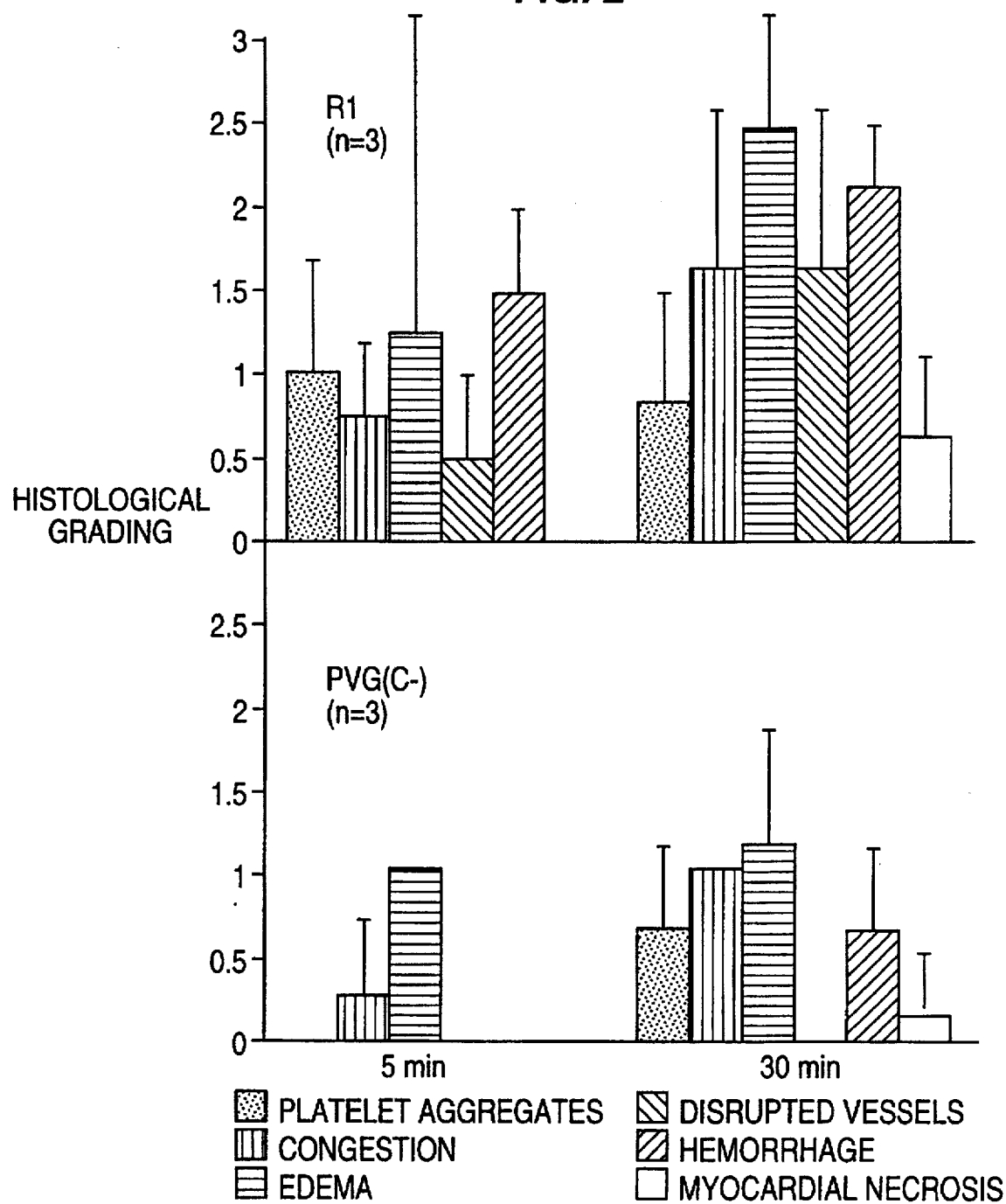
In FIG. 2, guinea pig cardiac xenografts harvested from R1 and PVG(C-) recipients 5 min. and 30 min. following reperfusion were evaluated for intravascular platelet aggregates, congestion, edema, disrupted vessels, interstitial hemorrhage and myocardial necrosis by histological grading from 1–3$^+$(H&E).

Histology: Cardiac xenografts that were hyperacutely rejected by R1 recipients (n=9) demonstrated intravascular platelet aggregation, edema, interstitial hemorrhage and myocardial necrosis by light microscopy. Xenografts that were removed 5 min. (n=3) and 30 min. (n=3) after transplantation to R1 recipients had significantly more intravascular platelet aggregation, vessel disruption and interstitial hemorrhage than xenografts removed from PVG(C–) recipients at the same time points (5 min., n=3; 30 min., n=3) as shown in FIG. 2. The xenografts that were rejected by PVG(C–) recipients at 2675+542 min. had little intravascular platelet aggregation and congestion, but had heavy infiltrations by polymorphonuclear leukocytes (PMN) and focal hemorrhage, that were first evident 24 h post perfusion. Representative guinea pig cardiac xenograft harvested from a PVG(C–) recipient 24 h following reperfusion showed numerous PMN attached to the endothelium of vessels, and migration of PMN into the interstitium (H & E X250).

The difference in the extent of platelet aggregation between xenografts harvested from R1 and PVG(C–) rats was made more evident by immunohistological evaluation, which demonstrated diffuse platelet aggregation within small vessels in xenografts of R1 recipients. Hyperacute rejection was characterized by intravascular platelet aggregation and interstitial hemorrhage, whereas xenografts rejected by PVG(C–) recipients were heavily infiltrated by granulocytes and monocytes but had patent vessels. These findings indicate that a deficiency in the terminal complement pathway at C6 prevents hyperacute rejection but allows an accelerated acute rejection that may be mediated by the generation of vasoactive and chemotactic C3a and C5 a.

Kinetics of C3 and C5 consumption

Figure 3:
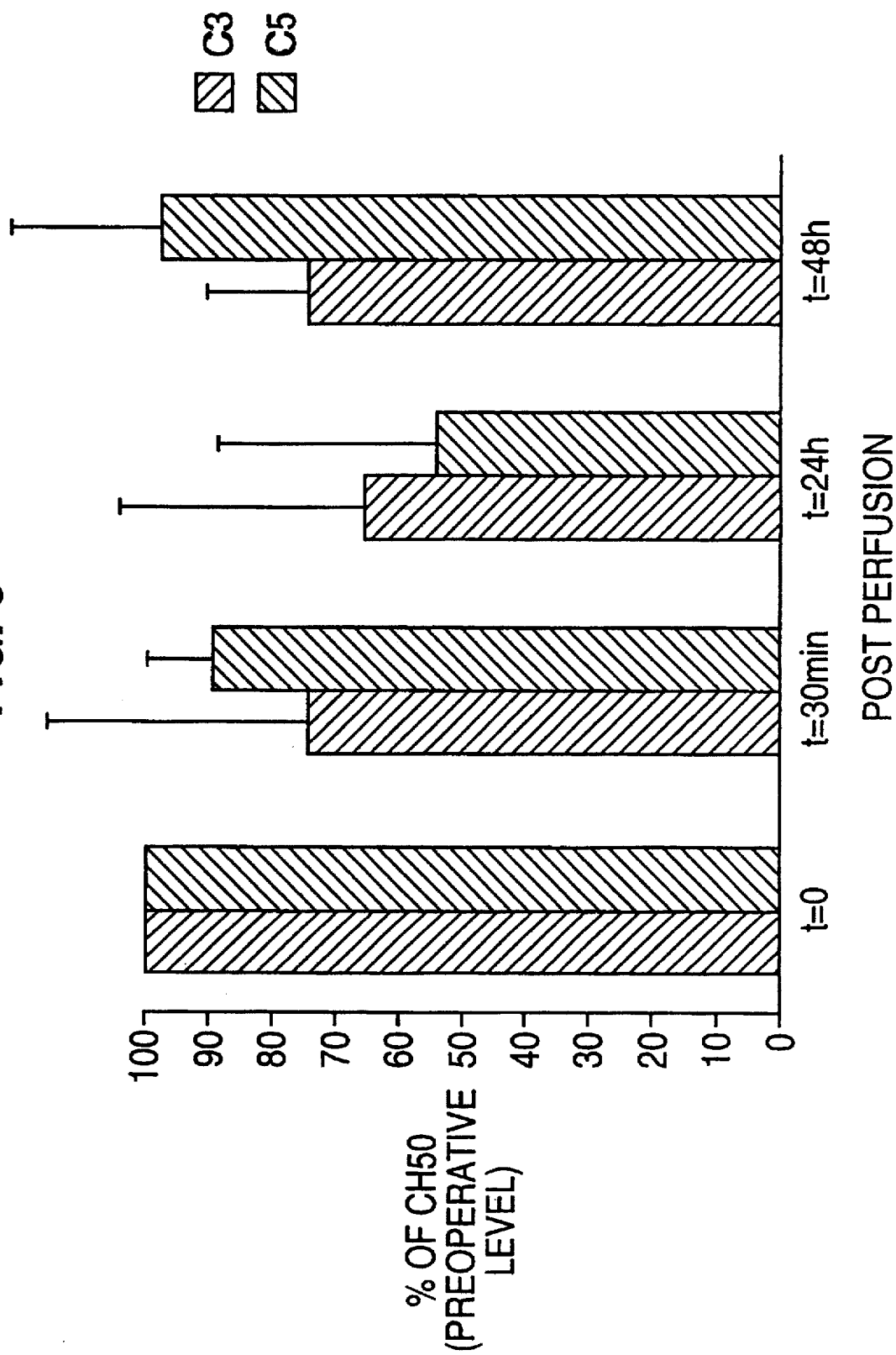
FIG. 3 shows the kinetics of C3 and C5 consumption in serum samples of PVG(C-) recipients (n=5). C3 and C5 were determined at t=0, t=30 min., t=24 h and t=48 h after transplantation of a guinea pig cardiac xenograft and expressed as the ability to reconstitute CH50 activity of C3 and C5 deficient human sera.

An isolated deficiency in C6 would not be expected to affect the activation and consumption of the early components of complement that are important mediators of inflammatory responses. Serum samples of five PVG(C–) guinea pig cardiac xenograft recipients were tested for C3 and C5 consumption 30 min., 24 h and 48 h post graft perfusion. Serum samples were collected from PVG(C–) rats by autologous heart puncture (n=5), 0, 30 min., 24 h and 48 h after they received a guinea pig cardiac xenograft. C3 and C5 levels in rat sera were measured by the ability to reconstitute the CH50 of C3 and C5 deficient human sera (Sigma, St. Louis, Mo.). Complement deficient human sera diluted 1:10 and PVG(C–) sera were mixed together and serially diluted. CH50 was determined as described above and expressed as the serum dilution yielding 50% maximal Hgb release. C3 and C5 serum levels decreased 30 min. post graft perfusion and reached their lowest levels 24 h post perfusion. By 48 h, when rejection was completed, C3 and C5 levels returned to preoperative serum levels (FIG. 3).

Immunofluorescence microscopy

Portions of cardiac xenografts collected at the time of sacrifice or rejection were embedded in gelatin and snap-frozen in a liquid nitrogen-immersed isopentane bath. Tissues were stored at –80° C. until 5–7 μm sections were prepared and mounted on gelatin coated glass microscope slides. After acetone fixation, sections were stained with FITC conjugated goat IgG specific for rat fibrinogen (Organo Teknika, Durham, N.C.) and rabbit IgG specific for rat platelets (Accurate). To distinguish tissue bound complement components as a result of complement fixation from passive trapping of serum components, tissue was treated with 2M NaCl solution before incubation with sheep anti-rat C3 Ab (The Binding Site, Birmingham, UK). The secondary FITC conjugated donkey anti-sheep IgG antibody (Jackson) was then applied. Sections were examined using a Zeiss D-7982 Oberkochen microscope fitted with an HBO-100 mercury-arc lamp.

IgM and complement deposition

Guinea pig cardiac xenografts rejected by PVG(C–) rats and PVG(C+) rats both bound rat IgM and C3 as detected by immunofluorescence with no qualitative difference in staining intensity noted between these two groups at 30 minutes, indicating that these early events in hyperacute rejection were not altered in the C6 deficient rats. IgM, and C3 were deposited on the endothelium of arterioles, capillaries and veins in guinea pig-to-rat cardiac xenografts. Guinea pig cardiac xenograft rejected by PVG(C+) within 29 min. and guinea pig cardiac xenograft beating for 30 min. in PVG (C–) recipient both showed vascular deposits of C3 relative to the control untransplanted guinea pig heart. Some interstitial deposition was found. Only minimal deposits of IgG were detected.

Supplemental Complement by Exogenous Serum transfer

To test whether exogenous complement could restore the ability to reject a guinea pig cardiac xenograft hyperacutely to PVG(C–) rats, 1 ml of fresh R1 serum was transferred to PVG(C–) recipients 45 min. and 105 min. post grafting.

Figure 4:
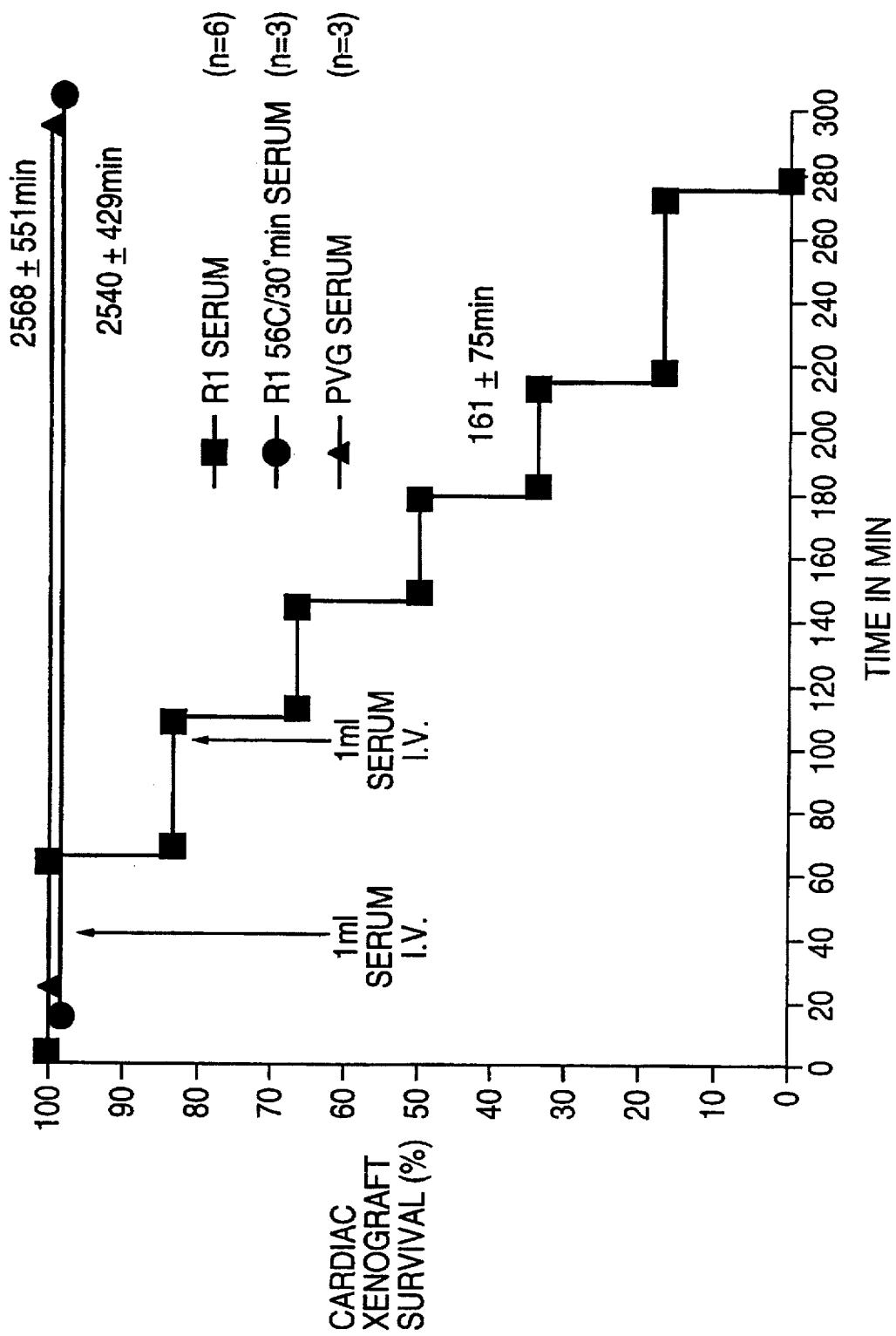
FIG. 4 shows guinea pig cardiac xenograft survival in PVG(C-) rats after post-grafting serum transfer. Transfer of fresh R1 serum (containing C6) caused hyperacute rejection of guinea pig cardiac xenografts within 3 hr. Transfer of heat inactivated R1 serum (56° C. for 30 min.) or fresh PVG serum did not affect the survival of guinea pig cardiac xenografts.

Serum transfer: 1 ml fresh or heat inactivated serum (56° C. for 30 min.) was transfused intravenously under halothane anesthesia via the dorsal penile vein, both 45 min. and 105 min. after graft reperfusion. The guinea pig cardiac xenografts, vigorously contracting prior to serum transfer, underwent hyperacute rejection within 116±75 min. (n=6) after the first injection of serum. Heat inactivation of R1 serum at 56° C. for 30 min. totally eliminated the capacity of R1 serum to transfer hyperacute rejection. These xenografts survived 2540±429 min. (n=3). Likewise transfer of 2 ml PVG(C–)serum did not affect guinea pig graft survival (2568+551 min.; n=3) as shown in FIG. 4.

Transfer of serum from R1 rats to PVG(C–) recipients with vigorously beating xenografts 45 min. post grafting caused hyperacute rejection of guinea pig cardiac xenografts within 116±75 min. (n=6). Transfer of fresh PVG(C–) serum or heat inactivated (56° complement for 30 min.) R1 serum did not induce hyperacute rejection (xenograft Survival of 2568±551, n=3 and 2540±429 min., n=3, respectively). Xenografts that were rejected after R1 serum transfer to PVG recipients (n =6) demonstrated vessel disruption, intravascular platelet aggregation, interstitial hemorrhage and edema, consistent with hyperacute rejection.

Example 2.

C6 Reconstitution by Liver Allograft in C6 Deficient Rats is Inhibited by Host Production of Antibody to C6

Evidence that the liver is the primary source of C6 production has been obtained by hepatocyte cultures, organ perfusion and allotyping of C6 after liver transplantation (LTX). In humans there is evidence also for local production of C6 by macrophages and other extra hepatic sources. To determine the relative contribution of C6 production by liver allografts, livers were transplanted between PVG (RT1$^c$) rats with normal complement activity [PVG(C+)] and PVG rats with a profound deficiency in C6 [PVG(C−)].

Complement activity as measured by the CH50 was detected within 24 h after grafting a liver from PVG(C+) into PVG(C−) rats (n=3). The complement activity was fully reconstituted to the CH50 of the PVG(C+) donor 7 days (d) post grafting, indicating the liver is a primary source of systemic C6 production. Complement activity was still present 14d and 21d post LTX, but diminished rapidly to undetectable levels at 28d and 100d after grafting.

To determine whether extra hepatic sources contributed to systemic C6 production, livers were orthotopically transplanted from PVG(C−) to PVG(C+) rats (n=3). The CH50 titer dropped from 117±34 to 48±17 within 1 day and reached a plateau after 21 days of 39±16, indicating that there is significant extra-hepatic C6 production in the rat, presumably by macrophages, monocytes and endothelial cells. Thus orthotopic LTX between C6 sufficient PVG(C+) and C6 deficient PVG(C−) rats indicates that the liver is a primary, but not sole source of C6.

Mixing experiments demonstrated that sera obtained 28d and 100d post LTX totally inhibit complement activity of PVG(C+) serum. A rat anti-rat polyclonal Ab was identified by Western Blotting in these sera. The rat anti-rat polyclonal Ab was of the IgG1 subclass and stained a double set of bands at 90kDa (identical to rat C6). These data suggest that transplants which produce complement components that express antigenic epitopes novel to the recipient can elicit antibody responses that suppress complement activity.

Example 3.

Polyclonal Rat Anti-rat C6 Antibody Fully Depletes C6 and Prevents Hyperacute Rejection of Cardiac Xenografts by the Lewis Rat Xenotransplantation between discordant species is presently avoided because of hyperacute rejection (HAR). A critical role of the complement (C) membrane attack complex C5b-9 (MAC) in mediating HAR has been defined in fully C6 deficient PVG(C−) (RT1$^c$) rats that reject guinea pig (GP) cardiac xenografts in a delayed tempo (45±9h); n=16) compared to C6 sufficient PVG(C+) hosts (0.5±2 h; n=6). This study investigated whether depletion of C6 from Lewis rats (LEW) with normal complement (C) levels by antibody (Ab) therapy prevents HAR.

Anti-C6 Antibody

A polyclonal rat anti-rat C6 Ab was induced by orthotopic liver transplantation (LTX) from congenic PVG(C+) to PVG(C−) recipients as described in Example 2. These liver grafts produced high levels of C6 that reconstituted the PVG(C−) hosts complement function by 7 days, but the recipients responded within 28d with an IgG1 Ab to rat C6. Sera obtained 28d and 100d post LTX totally inhibited complement activity of control sera in vitro when added in ratios of 1:2 and 1:5, respectively.

Antibody depletion of C6:

The in vivo kinetics of C6 depletion in two LEW rats was investigated by i.v. injection of 2 ml (≧20% of serum volume of 200 g rat) of the rat anti-rat-C6 Ab. Serum containing anti-rat C6 was collected by weekly bleeding 100d-135d post LTX and pooled. Blood samples were collected at t=−1 h, t=1 h, t=4 h, t=16 h relative to injection. Control LEW rats (n=3) received 2 ml of untreated PVG(C−) serum. I.V. injection of PVG(C−) serum did not change the hemolytic activity in the LEW rat. In rats injected with serum containing anti-rat-C6, hemolytic activity was undetectable 1 h after injection of the rat anti-rat C6 Ab (CH50≦2), but some activity was found 4 h after injection (CH50=8). The CH50 titer returned to pretreatment levels of 57±6 within 16 h after injection and the treatment was well tolerated. Reconstitution with purified human C6 in a dilution 1:100 restored the CH50 liter 1 h and 4 h after C6 depletion to pretreatment levels of 40±7 and 59±2 respectively.

C6 depletion suppresses hyperacute rejection

The effect of C6 depletion on xenograft survival was investigated by injecting LEW rats with 2 ml of rat anti-rat C6 before and 1 ml after reperfusion of the guinea pig cardiac xenograft. After treatment with a rat anti-rat C6 Ab LEW rats rejected guinea pig cardiac xenografts in 38±1 h (n=3). The same treatment with control sera of PVG(C−) did not prolong guinea pig cardiac xenograft survival in the LEW (1±0.5 h; n=3). These results demonstrate a significant effect of depletion of C6 on guinea pig cardiac xenograft survival in the LEW rat. These findings further indicate that treatment by C6 depletion may be beneficial to patients undergoing hyperacute rejection of xenografts or allografts.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

We claim:

1. A method of suppressing complement-dependent rejection of an organ transplant comprising administering an effective amount of an inhibitor of membrane attack complex formation (MAC formation inhibitor) to a recipient of a transplant organ wherein the inhibitor interferes with one or more binding steps in the sequential binding of complement component (C5b, C6, C7, C8, and C9, wherein the inhibitor is selected from the group consisting of a non-functional C6 analog, a non-functional C7 analog, an anti-C6 antibody and an anti-C7 antibody.

2. The method of claim 1, wherein said MAC formation inhibitor is an antibody that does not fix complement.

3. The method of claim 2, wherein said antibody that does not fix complement is selected from the group consisting of a monoclonal antibody of subclass IgG4, an Fab fragment and an F(ab')$_2$ fragment.

4. The method of claim 1, wherein said MAC formation inhibitor is administered in an amount sufficient to reduce the hemolytic activity of serum from the organ transplant recipient by at least about 10-fold.

5. The method of claim 1, wherein said MAC formation inhibitor is administered in an amount sufficient to reduce the hemolytic activity expressed in liter (CH50) of serum from the organ transplant recipient to less than 1:10.

6. The method of claim 1, wherein said organ transplant is selected from the group consisting of heart, kidney, lung, pancreas, liver, skin, and bone marrow.

7. The method of claim 1, wherein said organ transplant is a transfusion of blood or blood components selected from the group consisting of platelets, red blood cells, and leukocytes.

8. The method of claim 1, wherein said organ transplant is a xenograft, an allograft, an ABO incompatible organ or tissue, or an HLA incompatible organ or tissue.

9. The method of claim 1, wherein said complement-dependent rejection of organ transplant is hyperacute rejection.

10. The method of claim 1, wherein said complement-dependent rejection of an organ transplant is hyperacute rejection due to alternate pathway activation of complement initiated by ischemically damaged tissue in the organ used for transplantation.

11. A method of mitigating hyperacute graft rejection in a mammal receiving an incompatible organ transplant comprising administering a pharmaceutical composition containing an anti-C6 antibody or an anti-C7 antibody to said mammal in an amount sufficient to prevent hyperacute rejection.

12. The method of claim 11, wherein said incompatible organ transplant is an allograft, a graft with ABO incompatible antigens, a graft with HLA incompatible antigens, or a xenograft.

13. The method of claim 11, wherein said antibody is an antibody that does not fix complement.

14. The method of claim 13, wherein said antibody is selected from the group consisting of a monoclonal antibody of subclass IgG4, an Fab fragment and an F(ab')$_2$ fragment.

15. A method of suppressing complement-dependent rejection of organ transplants comprising infusing an isolated organ prior to transplant of said organ into an organ transplant recipient with an anti-C6 antibody or an anti-C7 antibody in an amount effective to suppress cell lysis initiated by formation of the C5b-C9 membrane attack complex.

16. The method of claim 15, wherein said antibody is an antibody that does not fix complement.

17. The method of claim 16, wherein said antibody is selected from the group consisting of a monoclonal antibody of subclass IgG4, an Fab fragment and an F(ab')$_2$ fragment.

* * * * *